United States Patent
Godden

(10) Patent No.: US 12,362,069 B2
(45) Date of Patent: Jul. 15, 2025

(54) METHOD, APPARATUS AND COMPUTER PROGRAM PRODUCT FOR PROVIDING A MULTI-OMICS FRAMEWORK FOR ESTIMATING TEMPORAL DISEASE TRAJECTORIES

(71) Applicant: Optum Services (Ireland) Limited, Dublin (IE)

(72) Inventor: Paul J. Godden, London (GB)

(73) Assignee: Optum Services (Ireland) Limited, Dublin (IE)

( * ) Notice: Subject to any disclaimer, the term of this patent is extended or adjusted under 35 U.S.C. 154(b) by 762 days.

(21) Appl. No.: 17/304,066

(22) Filed: Jun. 14, 2021

(65) Prior Publication Data
US 2022/0399120 A1 Dec. 15, 2022

(51) Int. Cl.
*G16H 50/30* (2018.01)
*G16B 25/10* (2019.01)
(Continued)

(52) U.S. Cl.
CPC ............ *G16H 50/30* (2018.01); *G16B 25/10* (2019.02); *G16B 50/30* (2019.02); *G16H 10/40* (2018.01); *G16H 10/60* (2018.01)

(58) Field of Classification Search
CPC ......... G16H 50/30; G16B 25/10; G16B 50/30
See application file for complete search history.

(56) References Cited

U.S. PATENT DOCUMENTS

2012/0101736 A1 4/2012 Dudley et al.
2017/0329904 A1 11/2017 Naughton et al.
(Continued)

FOREIGN PATENT DOCUMENTS

| CN | 108847288 A | 11/2018 |
| WO | 2019/246032 A1 | 12/2019 |
| WO | 2020/242976 A1 | 12/2020 |

OTHER PUBLICATIONS

Hurley, Killian et al.; "Single-cell time-series mapping of cell fate trajectories reveals an expanded developmental potential for human PSC-derived distal lung progenitors"; bioRxiv; Sep. 26, 2019; 73 pages (Year: 2019).*

(Continued)

*Primary Examiner* — Karlheinz R. Skowronek
*Assistant Examiner* — Emilie A Neulen
(74) *Attorney, Agent, or Firm* — Alston & Bird LLP

(57) ABSTRACT

Methods, apparatuses, systems, computing devices, computing entities, and/or the like are provided. An example method may include selecting at least one client profile data object from a plurality of client profile data objects; retrieving at least one initial transcriptome data object and at least one subsequent transcriptome data object associated with the at least one client profile data object; generating at least one dynamic multigraph data object based at least in part on the at least one initial transcriptome data object and the at least one subsequent transcriptome data object, the at least one subsequent transcriptome data object, and at least one clinical event data object; training a temporal graph network based at least in part on the at least one dynamic multigraph data object to generate a risk window prediction data object; and performing at least one data operation based at least in part on the risk window prediction data object.

17 Claims, 12 Drawing Sheets

(51) Int. Cl.
  *G16B 50/30* (2019.01)
  *G16H 10/40* (2018.01)
  *G16H 10/60* (2018.01)

(56) References Cited

U.S. PATENT DOCUMENTS

| | | |
|---|---|---|
| 2018/0174686 A1 | 6/2018 | Zaphrir et al. |
| 2019/0017119 A1 | 1/2019 | Khera et al. |
| 2019/0065670 A1 | 2/2019 | Yandell et al. |
| 2019/0345566 A1 | 11/2019 | Khera et al. |
| 2019/0371443 A1 | 12/2019 | Petricoin et al. |
| 2020/0027557 A1* | 1/2020 | Karow .............. G16H 50/50 |
| 2020/0167920 A1 | 5/2020 | Hall et al. |
| 2020/0251193 A1 | 8/2020 | White et al. |
| 2020/0283855 A1 | 9/2020 | Gutin et al. |
| 2022/0150123 A1* | 5/2022 | Kim .............. G06F 16/9024 |

OTHER PUBLICATIONS

"bvilhjal/LDpred," GitHub, Release 11, Version 1.0.8, Oct. 17, 2019, (6 pages), (online), [Retrieved from the Internet Jun. 23, 2021] <https://github.com/bvilhjal/ldpred>.

"Epitranscriptome," Wikipedia, (17 pages), (online), [Retrieved from the Internet Jun. 23, 2021] <https://en.wikipedia.org/wiki/Epitranscriptome>.

"Gene Signature," Wikipedia, (6 pages), (online), [Retrieved from the Internet Jun. 23, 2021] <https://en.wikipedia.org/wiki/Gene_signature>.

"Kaplan-Meier Estimator," Wikipedia, (9 pages), (online), [Retrieved from the Internet Jun. 23, 2021] <https://en.wikipedia.org/wiki/Kaplan%E2%80%93Meier_estimator>.

"Resource Overview," GTEx Portal (3 pages), (online), [Retrieved from the Internet Jun. 23, 2021] <https://gtexportal.org/home/>.

"Tissue Page," GTEx Portal, (3 pages), (online), [Retrieved from the Internet Jun. 23, 2021] <https://gtexportal.org/home/eqtls/tissue?tissueName=Lung>.

"True-Range Multilateration," Wikipedia, (8 pages), (online), [Retrieved from the Internet Jun. 23, 2021] <https://en.wikipedia.org/wiki/True-range_multilateration>.

Fritsche, Lars G. et al. "Association of Polygenic Risk Scores for Multiple Cancers in a Phenome-wide Study: Results from The Michigan Genomics Initiative," The American Journal of Human Genetics, vol. 102, Issue 6, Jun. 7, 2018, pp. 1048-1061, DOI: 10.1016/j.ajhg.2018.04.001.

Fritsche, Lars G. et al. "Exploring Various Polygenic Risk Scores For Skin Cancer in the Phenomes of the Michigan Genomics Initiative and the UK Biobank With a Visual Catalog: PRSWeb," PLoS Genetics, vol. 15, No. 6, Jun. 13, 2019, pp. 1-26, DOI: 10.1371/journal.pgen.1008202, e1008202.

Gainza, P. et al. "Deciphering Interaction Fingerprints From Protein Molecular Surfaces Using Geometric Deep Learning," bioRxiv, Apr. 11, 2019, (44 pages), DOI: 10.1101/606202.

Grover, Aditya et al. "node2vec: Scalable Feature Learning for Networks," In Proceedings of the 22nd ACM SIGKDD International Conference on Knowledge Discovery and Data Mining, arXiv:1607.00653 [cs.SI] Jul. 3, 2016, (10 pages). https://arxiv.org/abs/1607.00653.

Haque, Ashraful et al. "A Practical Guide to Single-Cell RNA-Sequencing For Biomedical Research and Clinical Applications," Genome Medicine, vol. 9, No. 75, Aug. 18, 2017, pp. 1-12, DOI: 10.1186/s13073-017-0467-4.

Hwang, Byungjin et al. "Single-Cell RNA Sequencing Technologies and Bioinformatics Pipelines," Experimental & Molecular Medicine, vol. 50, No. 96, Aug. 7, 2018, pp. 1-14, DOI: 10.1038/s12276-018-0071-8.

Jahchan, Nadine S. et al. "A Drug Repositioning Approach Identifies Tricyclic Antidepressants as Inhibitors of Small Cell Lung Cancer and Other Neuroendocrine Tumors," Cancer Discovery, vol. 3, No. 12, (25 pages), Dec. 2013, DOI: 10.1158/2159-8290.CD-13-0183.

Jensen, Anders Boeck et al. "Temporal Disease Trajectories Condensed From Population-Wide Registry Data Covering 6.2 Million Patients," Nature Communications, vol. 5, No. 4022, pp. 1-10, Jun. 24, 2014.

Jiang, Zhihua et al. "Whole Transcriptome Analysis With Sequencing—Methods, Challenges and Potential Solutions," Cellular and Molecular Life Sciences, vol. 72, No. 18, (25 pages), Sep. 2015, DOI: 10.1007/s00018-015-1934-y.

Kostakos, Vassilis. "Temporal Graphs," Physica A: Statistical Mechanics and its Applications, vol. 388, No. 6, Mar. 15, 2009, (23 pages), DOI: 10.1016/j.physa.2008.11.021.

Lanum, Cory L. "Visualizing Graph Data—Chapter 9. Dynamic Graphs: How to Show Data Over Time," Manning, Nov. 2016, (17 pages), ISBN 9781617293078, (online), [Retrieved from the Internet Jun. 23, 2021] <https://livebook.manning.com/book/visualizing-graph-data/chapter-9/>.

Lee, J.M. et al. "CAG Repeat Expansion in Huntington Disease Determines Age at Onset in a Fully Dominant Fashion," Neurology, vol. 78, No. 10, Mar. 6, 2012, pp. 690-695, DOI: 10.1212/WNL.0b013e318249f683.

Lupo, Giuseppe et al. "Molecular Signatures of the Aging Brain: Finding the Links Between Genes and Phenotypes," Neurotherapeutics, vol. 16, Jun. 3, 2019, pp. 543-553, DOI: 10.1007/s13311-019-00743-2.

Napoli, Claudio et al. "Differential Epigenetic Factors in the Prediction of Cardiovascular Risk in Diabetic Patients," European Heart Journal—Cardiovascular Pharmacotherapy, vol. 6, No. 4, Oct. 26, 2019, pp. 239-247, DOI: 10.1093/ehjcvp/pvz062.

Pai, Shraddha et al. "Patient Similarity Networks For Precision Medicine," Journal of Molecular Biology, vol. 430, Issue 18, Part A, Sep. 14, 2018, pp. 2924-2938, DOI: 10.1016/j.jmb.2018.05.037.

Rossi, Emanuele et al. "Temporal Graph Networks For Deep Learning on Dynamic Graphs," arXiv:2006.106373v3 [cs.LG] Oct. 9, 2020, (16 pages). https://arxiv.org/pdf/2006.10637.pdf.

Siggaard, Troels et al. "Disease Trajectory Browser For Exploring Temporal, Population-Wide Disease Progression Patterns in 7.2 Million Danish Patients," Nature Communications, vol. 11, No. 4952, Oct. 2, 2020, pp. 1-10, DOI: 10.1038/s41467-020-18682-4.

Tabak, Adam G. et al. "Prediabetes: a High-Risk State For Developing Diabetes," Lancet, vol. 379, No. 9833, (23 pages), Jun. 16, 2012, DOI: 10.1016/S0140-6736(12)60283-9.

Tang, Xiaoning et al. "The Single-Cell Sequencing: New Developments and Medical Applications," Cell & Bioscience, vol. 9, No. 53, pp. 1-9, Jun. 26, 2019. DOI: 10.1186/s13578-019-0314-y.

Vilhjalmsson, Bjarni J. "Modeling Linkage Disequilibrium Increases Accuracy of Polygenic Risk Scores," The American Journal of Human Genetics, vol. 97, Issue 4, Oct. 1, 2015, pp. 576-592, DOI: 10.1016/j.ajhg.2015.09.001.

Zitnik, Marinka et al. "Modeling Polypharmacy Side Effects With Graph Convolutional Networks," Bioinformatics, vol. 34, Issue 13, Jul. 1, 2018, pp. i457-i466. DOI: 10.1093/bioinformatics/bty294.

* cited by examiner

METHOD, APPARATUS AND COMPUTER PROGRAM PRODUCT FOR PROVIDING A MULTI-OMICS FRAMEWORK FOR ESTIMATING TEMPORAL DISEASE TRAJECTORIES

TECHNOLOGICAL FIELD

Embodiments of the present disclosure relate generally to improving computer and data system functionalities, such as, but not limited to, functionalities of data analytics and prediction systems. For example, various embodiments of the present disclosure may programmatically generate at least one dynamic multigraph data object based at least in part on at least one initial transcriptome data object, at least one subsequent transcriptome data object, and at least one clinical event data object, and may train a temporal graph network (TGN) based at least in part on the at least one dynamic multigraph data object to generate a risk window prediction data object.

BACKGROUND

Machine learning has great potential for providing various technical advancement and technical benefits not only in the field of computer science, but also in other associated technical fields and applications. Applicant has identified many technical challenges, deficiencies and problems associated with machine learning systems and methods.

BRIEF SUMMARY

In general, embodiments of the present disclosure provide methods, apparatuses, systems, computing devices, computing entities, and/or the like.

In accordance with various embodiments of the present disclosure, an apparatus is provided. The apparatus may comprise at least one processor and at least one non-transitory memory comprising a computer program code. The at least one non-transitory memory and the computer program code may be configured to, with the at least one processor, cause the apparatus to select at least one client profile data object from a plurality of client profile data objects based at least in part on at least one whole-genome sequence (WGS) data object related to a disease identifier and associated with the at least one client profile data object; retrieve at least one initial transcriptome data object and at least one subsequent transcriptome data object related to the disease identifier and associated with the at least one client profile data object; generate at least one dynamic multigraph data object based at least in part on the at least one initial transcriptome data object, the at least one subsequent transcriptome data object, and at least one clinical event data object; train a temporal graph network (TGN) based at least in part on the at least one dynamic multigraph data object to generate a risk window prediction data object associated with the disease identifier; and perform at least one data operation based at least in part on the risk window prediction data object. In some embodiments, the at least one subsequent transcriptome data object is associated with the at least one clinical event data object.

In some embodiments, the at least one WGS data object comprises at least one of at least one polygenic risk score (PRS) metadata related to the disease identifier or at least one combined PRS and phenome-wide association study (PRS-PheWAS) metadata related to the disease identifier. An example of PRS-PheWAS is described in *Association of Polygenic Risk Scores for Multiple Cancers in a Phenome-wide Study: Results from The Michigan Genomics Initiative* by Lars G. Fritsche et al. and published in the American Journal of Human Genetics (AJHG), volume 102, issue 6, pages 1048-1061, Jun. 7, 2018, the content of which is incorporated by reference in its entirety.

In some embodiments, the at least one initial transcriptome data object comprises at least one initial tissue-relevant transcriptome metadata associated with the disease identifier. In some embodiments, the at least one subsequent transcriptome data object comprises at least one subsequent tissue-relevant transcriptome metadata associated with the disease identifier.

In some embodiments, the at least one initial transcriptome data object comprises at least one initial single-cell ribonucleic acid (RNA) sequencing assay (scRNA-seq) metadata associated with the disease identifier. In some embodiments, the at least one subsequent transcriptome data object comprises at least one subsequent scRNA-seq assay metadata associated with the disease identifier.

In some embodiments, the at least one non-transitory memory and the computer program code are configured to, with the at least one processor, cause the apparatus to: calculate at least one differential expression metadata based at least in part on the at least one initial transcriptome data object and the at least one subsequent transcriptome data object. In some embodiments, the at least one non-transitory memory and the computer program code are configured to, with the at least one processor, cause the apparatus to generate the at least one dynamic multigraph data object based at least in part on the at least one differential expression metadata.

In some embodiments, for a client profile data object of the at least one client profile data object, a corresponding initial transcriptome data object of the at least one initial transcriptome data object and a corresponding WGS data object of the at least one WGS data object are associated with an initial temporal identifier.

In some embodiments, for the client profile data object of the at least one client profile data object, a corresponding subsequent transcriptome data object of the at least one subsequent transcriptome data object and a corresponding clinical event data object of the at least one clinical event data object are associated with a corresponding subsequent temporal identifier.

In some embodiments, the at least one non-transitory memory and the computer program code are configured to, with the at least one processor, cause the apparatus to generate at least one dynamic multigraph data object based further on the initial temporal identifier and the corresponding subsequent.

In some embodiments, the risk window prediction data object comprises an estimated lower bound metadata and an estimated upper bound metadata associated with the disease identifier.

In some embodiments, the at least one non-transitory memory and the computer program code are configured to, with the at least one processor, cause the apparatus to: retrieve at least one validated onset temporal metadata associated with the at least one client profile data object and the disease identifier. In some embodiments, the at least one non-transitory memory and the computer program code are configured to, with the at least one processor, cause the apparatus to train the TGN based at least in part on the at least one validated onset temporal metadata.

In some embodiments, when performing the at least one data operation based at least in part on the risk window prediction data object, the at least one non-transitory memory and the computer program code are configured to, with the at least one processor, cause the apparatus to: transmit the risk window prediction data object to a client computing entity.

In some embodiments, the at least one non-transitory memory and the computer program code are configured to, with the at least one processor, cause the apparatus to: retrieve a second initial transcriptome data object and a second subsequent transcriptome data object related to the disease identifier and associated with a second client profile data object of the at least one client profile data object; generate a second dynamic multigraph data object based at least in part on the second initial transcriptome data object, the second subsequent transcriptome data object, and the second clinical event data object; and generate a second risk window prediction data object based at least in part on providing the second dynamic multigraph data object to the TGN. In some embodiments, the second subsequent transcriptome data object is associated with a second clinical event data object.

In accordance with various embodiments of the present disclosure, a computer-implemented method is provided. The computer-implemented method may comprise selecting at least one client profile data object from a plurality of client profile data objects based at least in part on at least one whole-genome sequence (WGS) data object related to a disease identifier and associated with the at least one client profile data object; retrieving at least one initial transcriptome data object and at least one subsequent transcriptome data object related to the disease identifier and associated with the at least one client profile data object; generating at least one dynamic multigraph data object based at least in part on the at least one initial transcriptome data object, the at least one subsequent transcriptome data object, and the at least one clinical event data object; training a TGN based at least in part on the at least one dynamic multigraph data object to generate a risk window prediction data object associated with the disease identifier; and performing at least one data operation based at least in part on the risk window prediction data object. In some embodiments, the at least one subsequent transcriptome data object is associated with at least one clinical event data object.

In accordance with various embodiments of the present disclosure, a computer program product is provided. The computer program product may comprise at least one non-transitory computer-readable storage medium having computer-readable program code portions stored therein. The computer-readable program code portions may comprise an executable portion configured to select at least one client profile data object from a plurality of client profile data objects based at least in part on at least one whole-genome sequence (WGS) data object related to a disease identifier and associated with the at least one client profile data object; retrieve at least one initial transcriptome data object and at least one subsequent transcriptome data object related to the disease identifier and associated with the at least one client profile data object; generate at least one dynamic multigraph data object based at least in part on the at least one initial transcriptome data object, the at least one subsequent transcriptome data object, and the at least one clinical event data object; train a TGN based at least in part on the at least one dynamic multigraph data object to generate a risk window prediction data object associated with the disease identifier; and perform at least one data operation based at least in part on the risk window prediction data object. In some embodiments, the at least one subsequent transcriptome data object is associated with at least one clinical event data object.

The above summary is provided merely for purposes of summarizing some example embodiments to provide a basic understanding of some aspects of the disclosure. Accordingly, it will be appreciated that the above-described embodiments are merely examples. It will be appreciated that the scope of the disclosure encompasses many potential embodiments in addition to those here summarized, some of which will be further described below.

BRIEF DESCRIPTION OF THE SEVERAL VIEWS OF THE DRAWING(S)

Having thus described the disclosure in general terms, reference will now be made to the accompanying drawings, which are not necessarily drawn to scale, and wherein:

Figure 3:
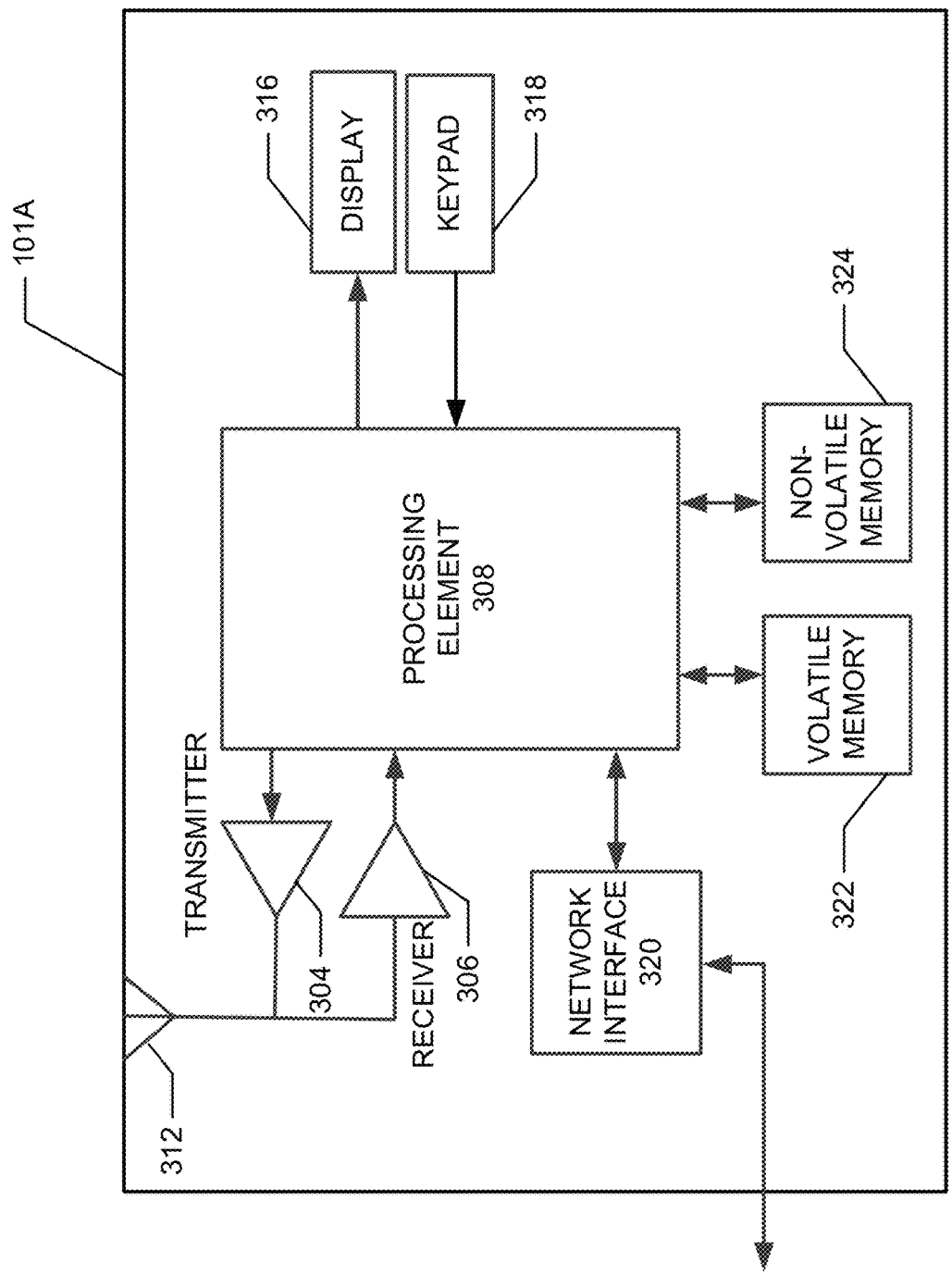

FIG. 3 is a schematic representation of an example client computing entity in accordance with various embodiments of the present disclosure; and FIGS. 4, 5, 6, 7, 8, 9, 10, 11, and 12 provide example flowcharts and diagrams illustrating example steps, processes, procedures, and/or operations associated with an example data object generating platform/system in accordance with various embodiments of the present disclosure.

DETAILED DESCRIPTION OF SOME EXAMPLE EMBODIMENTS

Various embodiments of the present disclosure now will be described more fully hereinafter with reference to the accompanying drawings, in which some, but not all embodiments of the disclosure are shown. Indeed, this disclosure may be embodied in many different forms and should not be construed as limited to the embodiments set forth herein; rather, these embodiments are provided so that this disclosure will satisfy applicable legal requirements. The term "or" (also designated as "/") is used herein in both the alternative and conjunctive sense, unless otherwise indicated. The terms "illustrative" and "exemplary" are used to be examples with no indication of quality level. Like numbers refer to like elements throughout. The phrases "in one embodiment," "according to one embodiment," and/or the like generally mean that the particular feature, structure, or characteristic following the phrase may be included in at least one embodiment of the present disclosure and may be included in more than one embodiment of the present disclosure (importantly, such phrases do not necessarily refer to the same embodiment).

I. Computer Program Products, Methods, and Computing Entities

Embodiments of the present disclosure may be implemented as computer program products that comprise articles of manufacture. Such computer program products may include one or more software components including, for example, applications, software objects, methods, data structures, and/or the like. A software component may be coded in any of a variety of programming languages. An illustrative programming language may be a lower-level programming language such as an assembly language associated with a particular hardware architecture and/or operating system platform/system. A software component comprising assembly language instructions may require conversion into executable machine code by an assembler prior to execution by the hardware architecture and/or platform/system. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

Additionally, or alternatively, embodiments of the present disclosure may be implemented as a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media may include all computer-readable media (including volatile and non-volatile media).

In one embodiment, a non-volatile computer-readable storage medium may include a floppy disk, flexible disk, hard disk, solid-state storage (SSS) (e.g., a solid-state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present disclosure may also be implemented as methods, apparatuses, systems, computing devices, computing entities, and/or the like. As such, embodiments of the present disclosure may take the form of a data structure, apparatus, system, computing device, computing entity, and/or the like executing instructions stored on a computer-readable storage medium to perform certain steps or operations. Thus, embodiments of the present disclosure may also take the form of an entirely hardware embodiment, an entirely computer program product embodiment, and/or an embodiment that comprises combination of computer program products and hardware performing certain steps or operations.

Embodiments of the present disclosure are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

II. Exemplary System Architecture

Figure 1:
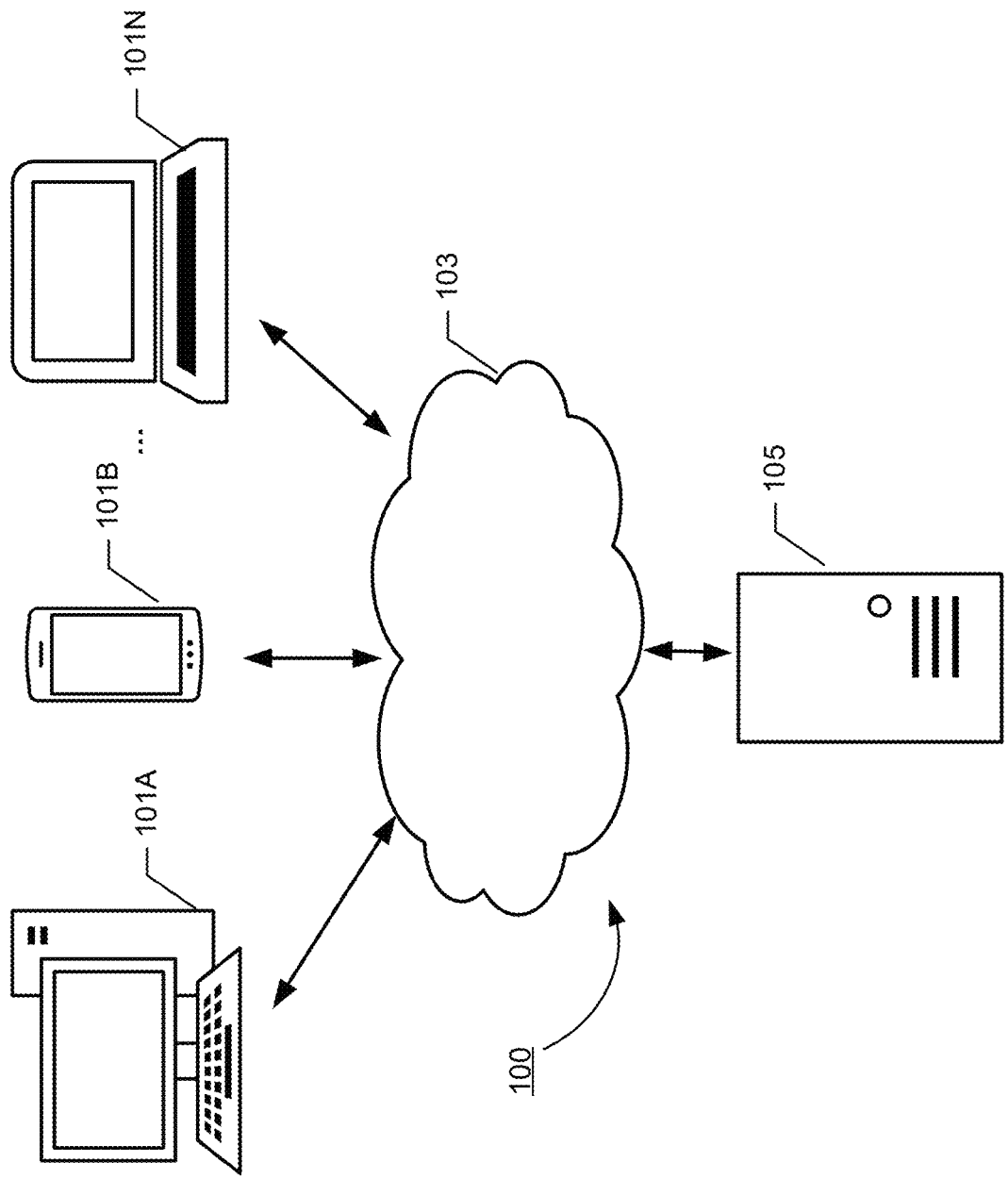
FIG. 1 is a diagram of an example data object generating platform/system that can be used in accordance with various embodiments of the present disclosure.

FIG. 1 provides an illustration of a data object generating platform/system 100 that can be used in conjunction with various embodiments of the present disclosure. As shown in FIG. 1, the data object generating platform/system 100 may comprise one or more data object computing entities 105, one or more client computing entities 101A, 101B, . . . 101N, and one or more networks 103. Each of the components of the data object generating platform/system 100 may be in electronic communication with, for example, one another over the same or different wireless or wired networks 103 including, for example, a wired or wireless Personal Area Network (RAN), Local Area Network (LAN), Metropolitan Area Network (MAN), Wide Area Network (WAN), and/or the like. Additionally, while FIG. 1 illustrates certain system entities as separate, standalone entities, the various embodiments are not limited to this particular architecture.

a. Exemplary Data Object Computing Entity

Figure 2:
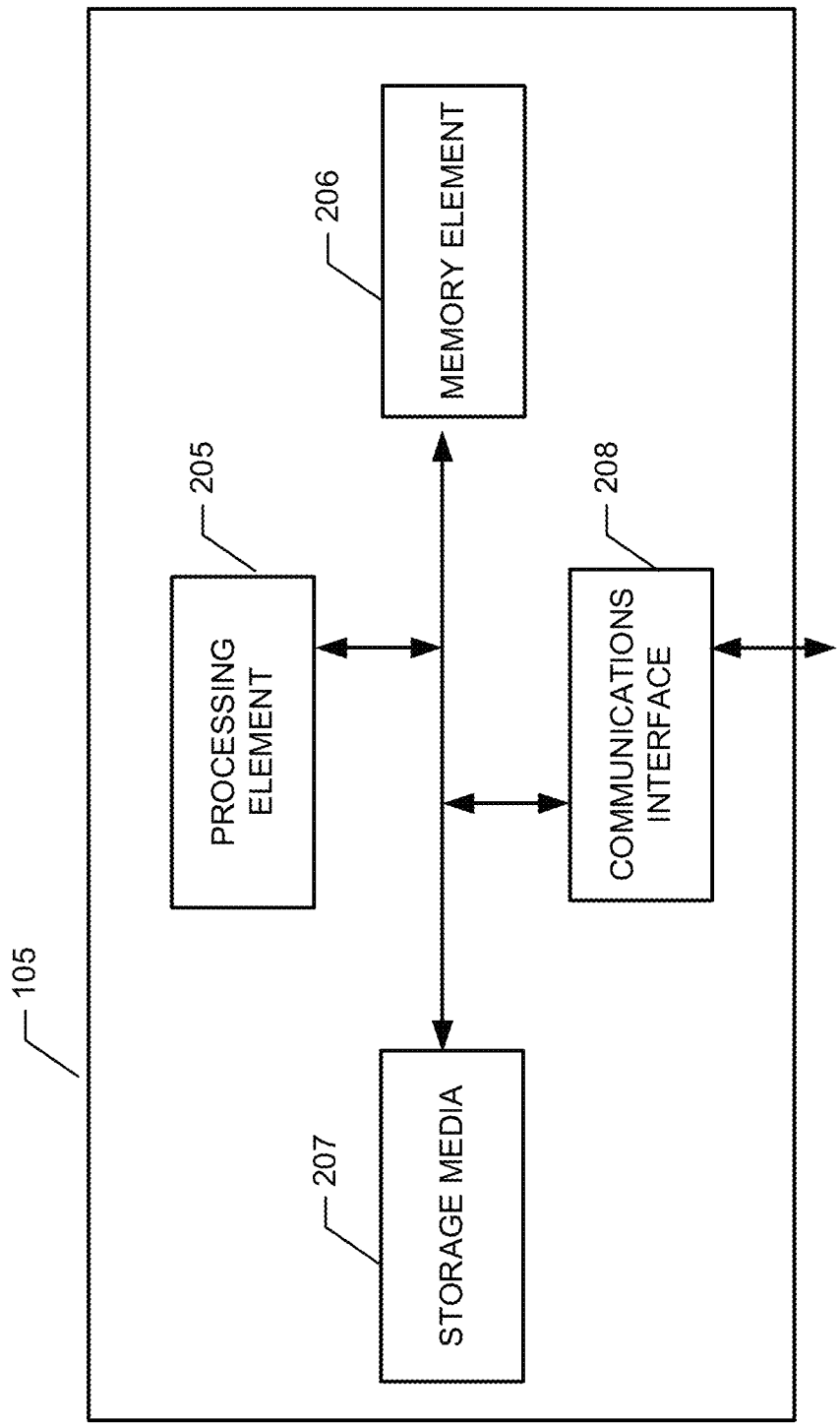
FIG. 2 is a schematic representation of an example data object computing entity in accordance with various embodiments of the present disclosure.

FIG. 2 provides a schematic of a data object computing entity 105 according to one embodiment of the present disclosure. In general, the terms computing entity, entity, device, system, and/or similar words used herein interchangeably may refer to, for example, one or more computers, computing entities, desktop computers, mobile phones, tablets, phablets, notebooks, laptops, distributed systems, items/devices, terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein. In one embodiment, these functions, operations, and/or processes can be performed on data, content, information, and/or similar terms used herein.

As indicated, in one embodiment, the data object computing entity 105 may also include one or more network and/or communications interface 208 for communicating with various computing entities, such as by communicating data, content, information, and/or similar terms used herein that can be transmitted, received, operated on, processed, displayed, stored, and/or the like. For instance, the data object computing entity 105 may communicate with other data object computing entities 105, one or more client computing entities 101A-101N, and/or the like.

As shown in FIG. 2, in one embodiment, the data object computing entity 105 may include or be in communication with one or more processing elements (for example, processing element 205) (also referred to as processors, processing circuitry, and/or similar terms used herein interchangeably) that communicate with other elements within the data object computing entity 105 via a bus, for example, or network connection. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present disclosure when configured accordingly.

In one embodiment, the data object computing entity 105 may further include or be in communication with volatile media (also referred to as volatile storage, memory, memory storage, memory circuitry and/or similar terms used herein interchangeably). In one embodiment, the volatile storage or memory may also include one or more memory element 206 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory element 206 may be used to store at least portions of the databases, database instances, database management system entities, data, applications, programs, program modules, scripts, source code, object code, byte code, compiled code, interpreted code, machine code, executable instructions, and/or the like being executed by, for example, the processing element 205 as shown in FIG. 2 and/or the processing element 308 as described in connection with FIG. 3. Thus, the databases, database instances, database management system entities, data, applications, programs, program modules, scripts, source code, object code, byte code, compiled code, interpreted code, machine code, executable instructions, and/or the like may be used to control certain aspects of the operation of the data object computing entity 105 with the assistance of the processing element 205 and operating system.

In one embodiment, the data object computing entity 105 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or storage media 207 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or storage media 207 may store databases, database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably and in a general sense to refer to a structured or unstructured collection of information/data that is stored in a computer-readable storage medium.

Storage media 207 may also be embodied as a data storage device or devices, as a separate database server or servers, or as a combination of data storage devices and separate database servers. Further, in some embodiments, storage media 207 may be embodied as a distributed repository such that some of the stored information/data is stored centrally in a location within the system and other information/data is stored in one or more remote locations. Alternatively, in some embodiments, the distributed repository may be distributed over a plurality of remote storage locations only. An example of the embodiments contemplated herein would include a cloud data storage system maintained by a third-party provider and where some or all of the information/data required for the operation of the recovery prediction system may be stored. Further, the information/data required for the operation of the recovery prediction system may also be partially stored in the cloud data storage system and partially stored in a locally maintained data storage system. More specifically, storage media 207 may encompass one or more data stores configured to store information/data usable in certain embodiments.

As indicated, in one embodiment, the data object computing entity 105 may also include one or more network and/or communications interface 208 for communicating with various computing entities, such as by communicating data, content, information, and/or similar terms used herein interchangeably that can be transmitted, received, operated on, processed, displayed, stored, and/or the like. For instance, the data object computing entity 105 may communicate with computing entities or communication interfaces of other data object computing entities 105, client computing entities 101A-101N, and/or the like.

As indicated, in one embodiment, the data object computing entity 105 may also include one or more network and/or communications interface 208 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the data object computing entity 105 may be configured to communicate via wireless external communication networks using any of a variety of protocols, such as general packet radio service (GPRS), Universal Mobile Telecommunications System (UMTS), Code Division Multiple Access 1900 (CDMA1900), CDMA1900 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), Institute of Electrical and Electronics Engineers (IEEE) 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol. The data object computing entity 105 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

As will be appreciated, one or more of the data object computing entity's components may be located remotely from components of other data object computing entities 105, such as in a distributed system. Furthermore, one or more of the components may be aggregated and additional components performing functions described herein may be included in the data object computing entity 105. Thus, the data object computing entity 105 can be adapted to accommodate a variety of needs and circumstances.

b. Exemplary Client Computing Entity

FIG. 3 provides an illustrative schematic representative of one of the client computing entities 101A to 101N that can be used in conjunction with embodiments of the present disclosure. As will be recognized, the client computing entity may be operated by an agent and include components and features similar to those described in conjunction with the data object computing entity 105. Further, as shown in FIG. 3, the client computing entity may include additional components and features. For example, the client computing entity 101A can include an antenna 312, a transmitter 304 (e.g., radio), a receiver 306 (e.g., radio), and a processing element 308 that provides signals to and receives signals from the transmitter 304 and receiver 306, respectively. The signals provided to and received from the transmitter 304 and the receiver 306, respectively, may include signaling information/data in accordance with an air interface standard of applicable wireless systems to communicate with various entities, such as a data object computing entity 105, another client computing entity 101A, and/or the like. In this regard, the client computing entity 101A may be capable of operating with one or more air interface standards, communication protocols, modulation types, and access types. More particularly, the client computing entity 101A may comprise a network interface 320, and may operate in accordance with any of a number of wireless communication standards and protocols. In a particular embodiment, the client computing entity 101A may operate in accordance with multiple wireless communication standards and protocols, such as GPRS, UMTS, CDMA1900, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the client computing entity 101A can communicate with various other entities using Unstructured Supplementary Service data (USSD), Short Message Service (SMS), Multimedia Messaging Service (MMS), Dual-Tone Multi-Frequency (DTMF) Signaling, Subscriber Identity Module Dialer (SIM dialer), and/or the like. The client computing entity 101A can also download changes, add-ons, and updates, for instance, to its firmware, software (e.g., including executable instructions, applications, program modules), and operating system.

According to one embodiment, the client computing entity 101A may include location determining aspects, devices, modules, functionalities, and/or similar words used herein interchangeably. For example, the client computing entity 101A may include outdoor positioning aspects, such as a location module adapted to acquire, for example, latitude, longitude, altitude, geocode, course, direction, heading, speed, UTC, date, and/or various other information/data. In one embodiment, the location module can acquire data, sometimes known as ephemeris data, by identifying the number of satellites in view and the relative positions of those satellites. The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. Alternatively, the location information/data/data may be determined by triangulating the position in connection with a variety of other systems, including cellular towers, Wi-Fi access points, and/or the like. Similarly, the client computing entity 101A may include indoor positioning aspects, such as a location module adapted to acquire, for example, latitude, longitude, altitude, geocode, course, direction, heading, speed, time, date, and/or various other information/data. Some of the indoor aspects may use various position or location technologies including Radio-Frequency Identification (RFID) tags, indoor beacons or transmitters, Wi-Fi access points, cellular towers, nearby computing devices (e.g., smartphones, laptops) and/or the like. For instance, such technologies may include iBeacons, Gimbal proximity beacons, Bluetooth Low Energy (BLE) transmitters, Near Field Communication (NFC) transmitters, and/or the like. These indoor positioning aspects can be used in a variety of settings to determine the location of someone or something to within inches or centimeters.

The client computing entity 101A may also comprise a user interface comprising one or more user input/output interfaces (e.g., a display 316 and/or speaker/speaker driver coupled to a processing element 308 and a touch screen, keyboard, mouse, and/or microphone coupled to a processing element 308). For example, the user output interface may be configured to provide an application, browser, user interface, dashboard, webpage, and/or similar words used herein interchangeably executing on and/or accessible via the client computing entity 101A to cause display or audible presentation of information/data and for user interaction therewith via one or more user input interfaces. The user output interface may be updated dynamically from communication with the data object computing entity 105. The user input interface can comprise any of a number of devices allowing the client computing entity 101A to receive data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the client computing entity 101A and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the client computing entity 101A can collect information/data, user interaction/input, and/or the like.

The client computing entity 101A can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, data, applications, programs, program modules, scripts, source code, object code, byte code, compiled code, interpreted code, machine code, executable instructions, and/or the like to implement the functions of the client computing entities 101A-101N.

c. Exemplary Networks

In one embodiment, the networks 103 may include, but are not limited to, any one or a combination of different types of suitable communications networks such as, for example, cable networks, public networks (e.g., the Internet), private networks (e.g., frame-relay networks), wireless networks, cellular networks, telephone networks (e.g., a public switched telephone network), or any other suitable private and/or public networks. Further, the networks 103 may have any suitable communication range associated therewith and may include, for example, global networks (e.g., the Internet), MANs, WANs, LANs, or PANs. In addition, the networks 103 may include medium over which network traffic may be carried including, but not limited to, coaxial cable, twisted-pair wire, optical fiber, a hybrid fiber coaxial (HFC) medium, microwave terrestrial transceivers, radio frequency communication mediums, satellite communication mediums, or any combination thereof, as well as a variety of network devices and computing platforms/systems provided by network providers or other entities.

Further, the networks 103 may utilize a variety of networking protocols including, but not limited to, TCP/IP based networking protocols. In some embodiments, the protocol is a custom protocol of JavaScript Object Notation (JSON) objects sent via a WebSocket channel. In some embodiments, the protocol is JSON over RPC, JSON over REST/HTTP, and/or the like.

III. Exemplary Operation

Reference will now be made to FIGS. 4, 5, 6, 7, 8, 9, 10, 11, and 12, which provide flowcharts and diagrams illustrating example steps, processes, procedures, and/or operations associated with a data object generating platform/system and/or a data object computing entity in accordance with various embodiments of the present disclosure.

As described herein, various embodiments of the present disclosure may generate a risk window prediction data object that indicates a predicted/estimated temporal window of the most likely onset of symptomatic disease. During the training of various machine leaning models described herein, the predicted/estimated temporal window is the target variable by which the accuracy of various examples described herein are measured. As will be recognized, embodiments of the present disclosure are not limited to these examples only.

a. Overview

As described above, machine learning has great potential for providing various technical advancement and technical benefits not only in the field of computer science, but also in other associated technical fields and applications.

For example, a polygenic risk score ("PRS") (also referred to as a polygenic score, or genome-wide score) is a number that may indicate a patient's risk or propensity to a particular disease that may have a significant genetic risk component. For example, an example PRS may be calculated by adding up a patient's risk alleles, with each risk alleles multiplied by weights that are directed from data source(s) such, as, but not limited to, genome-wide associated study (GWAS) data. In other words, an example PRS may summarize estimated effect(s) of genetic variants on a patient's phenotype as a weighted sum of trait-associated alleles. In calculating an example PRS, the reported effect sizes for those alleles may be considered, and the example PRS may be normalized by tuning for the total number of risk alleles and effect sizes that have been assessed.

In some examples, if a patient has an accurate, clinically-validated PRS for a given condition or disease, and a patient has his or her genome sequenced, the result would be an estimated lifetime risk of condition or disease occurrence, but not the timescale or time frame for when disease onset would occur. As such, one of the most outstanding challenges in contemporary clinical genetics is that risk scoring cannot predict or determine when a disease or a condition is likely to occur in a patient.

Many computer systems and associated methods fail to overcome such challenges.

For example, in general and for many conditions that have multiple genetic variants that contribute to disease causality, there are few to no indicators of disease onset. Examples such as relative risk and hazard ratio may estimate the conditional failure of an event (e.g. survival time). However, these statistical approaches do not take in to account genetic data. In the case of Kaplan-Meier analysis, such approaches only estimate median survival times rather than a particular individual's temporal risk trajectory for symptomatic disease onset.

As another example, many computer systems rely solely on the PRSs in conducting analysis of data associated with a patient, and thereby fail to capture any temporal information associated with the progression of a disease or a condition and are unable to estimate an approximate age of onset for diseases and conditions that may have a significant genetic risk component. Additionally, in conducting analysis, many computer systems and methods rely on a static graph representation that retains no temporal information, thereby fail to generate any estimate of an approximate time/age of onset for diseases and conditions. As such, the lack of analytical methods for estimating an approximate time/age of onset for diseases/conditions that have a significant genetic risk component has been hindering the development of both computer science and disease prediction.

Various embodiments of the present disclosure overcome such challenges, and provide technical advancement and technical benefits in not only the field of computer science, but also in at least the field of disease prediction, and provide technical improvements on computer and data system functionalities, such as, but not limited to, functionalities of data analytics and prediction systems.

For example, various embodiments of the present disclosure may provide a multi-omics framework that utilizes such as, but not limited to, clinical event data objects associated with a client profile data object in order to derive a risk window prediction data object indicating a "risk window" for when the disease or conditions under consideration may become fully symptomatic in a patient/client.

Various embodiments of the present disclosure may generate a data structure referred to as "dynamic multigraph data object" that utilizes evolving graph representations of longitudinal clinical data for a selected cohort of patients/clients who are determined to be at lifetime risk of a specified disease. In some embodiments, a computing entity may retrieve data objects, such as, but not limited to, whole-genome sequence (WGS) data objects, initial transcriptome data objects, subsequent transcriptome data objects, and/or clinical event data objects associated with the selected cohort, and may utilize such data objects to generate a dynamic multigraph data object, details of which are described herein. For example, the computing entity may formulate a base risk score metadata (from the WGS data objects), subsequent clinical event data objects and associated scRNA-seq assay metadata (from the transcriptome data objects), and may compute differential expression metadata indicating differential tissue expression to form an example dynamic multigraph data object, details of which are described herein. In various embodiments, an example dynamic multigraph data object allows these data objects to be represented in a way as a multigraph that grows and evolves over time, which captures temporal information and overcomes above mentioned technical challenges (for example, in contrast with a static graph).

In some embodiments, the prediction of time period of a disease being onset is performed via a specialized machine learning algorithm, suitable for an analysis of data that are stored in a dynamically-evolving graph database (for example, the dynamic multigraph data object described herein). In some embodiments, the specialized machine learning algorithm may be in the form of a temporal graph networks (TGN), which is a type of graph machine learning algorithm that is highly effective on dynamic multigraphs.

In some embodiments, a computing entity may train the TGN on the dynamic multigraph data object that is a continuous dynamic multigraph representing the clinical event(s) and associated scRNA-seq assay metadata. In some embodiments, each relevant clinical event triggers acquisition of relevant tissue scRNA-seq assay metadata, which may then be used to establish the differential expression state from a baseline or initial scRNA-seq assay metadata. In some embodiments, a computing entity may implement appropriate graph embeddings (such as, but not limited to, Node2Vec or similar representations) to transform these data objects associated with the selected cohort of patients/clients to a data structure (e.g. a dynamic multigraph data object) that is suitable for ingestion by the TGN, and thereby enabling the TGN to perform data analysis and prediction across the entire cohort.

In some embodiments, the TGN may generate a prediction of the "risk window" in the form of a risk window prediction data object. In some embodiments, the risk window prediction data object comprises an estimated lower bound metadata and an estimated upper bound metadata defining the most likely symptomatic onset time period of the disease in question. Because the differential expression of the disease tissue(s) evolve in some temporal sense towards a final state for the disease in question, tracking these intermediate "expression signatures" may permit estimation of the time for disease onset. In this way, starting from the most robust risk score available, various embodiments of the present disclosure provide a framework to estimate the time period for disease onset, following the trajectory of clinical events and differential expression(s).

Various embodiments of the present disclosure may take large-scale data and create as narrow a window for the symptomatic onset of a specific disease as possible, rather than apply median estimates derived from a specific cohort. In some embodiments, the PRS-PheWAS approach with clinical event analysis prompting scRNA-seq assaying to produce a time series of differential gene expression, which may then be compared against similar groups of patients. In some embodiments, a TGN is applied to clinical data and used for clinical risk scoring.

While the description above provides some example technical challenges and difficulties that various embodiments of the present disclosure overcome, it is note that various embodiments of the present disclosure may overcome various other technical challenges and difficulties.

For example, many analyses and approaches of population-level disease multi-morbidity trajectories are faced with many technical challenges and difficulties, and various embodiments of the present disclosure may overcome such challenges and provide improvements on these analysis and approaches.

As an example, many population-level analyses and approaches aim to group together corresponding diseases to understand multi-morbid conditions, rather than starting with a defined risk score for one condition and then estimating the temporal window of most likely onset in accordance with various embodiments of the present disclosure.

As another example, many population-level analyses and approaches fail to utilize any kind of genomics data, and did not use any risk score. Many population-level analyses and approaches do not use PRS-PheWAS in conjunction with clinical event-aligned differential expression data to perform integrated risk scoring. Many population-level analyses and approaches were conducted on the patient population of specific regions that have a longitudinal EMR and may have to rely on a nation-wide EMR system. In contrast, various embodiments of the present disclosure provide the genomics basis to be population-agnostic and additionally reply upon genomics data (e.g. WGS data objects, transcriptome data objects) to refine the "risk window" estimation. Various embodiments of the present discourse may also cast data in the form of graphs, either static or dynamic, and apply a TGN.

As another example, many population-level analyses and approaches do not attempt to estimate a temporal "risk window," but instead suggests the epigenomic biomarkers will be of important in detection of diabetic patients who would be at an increased risk of cardiovascular disease. Many population-level analyses and approaches also fail to utilize PRS or PRS-PheWAS, which are distinct from the use of expression as a prognostic gene signature. In contrast, various embodiments of the present disclosure may utilize PRS or PRS-PheWAS and use expression as a prognostic gene signature to estimate a temporal "risk window."

Accordingly, various embodiments of the present disclosure provide technical advancement and technical benefits in not only the field of computer science, but also at least the field of disease prediction, and provide technical improvements on computer and data system functionalities, such as, but not limited to, through generating a dynamic multigraph data object that captures temporal information, improving the functionalities of a TGN through training the TGN using the dynamic multigraph data object, and generating a risk window prediction data object indicating the timescale for when disease onset would occur.

b. Definitions

In the present disclosure, the term "data object" refers to a data structure that represents, indicates, stores and/or comprises data and/or information. In some embodiments, a data object may be in the form of one or more regions in one or more data storage devices (such as, but not limited to, a computer-readable storage medium) that comprise one or more values (such as, but not limited to, one or more identifiers, one or more metadata, and/or the like). In some embodiments, an example data object may comprise or be associated with one or more identifiers, one or more metadata, and/or one or more other data objects.

In accordance with various embodiments of the present disclosure, data objects may be characterized based at least in part on the data and/or information associated with the data object. Examples of data objects may include, but not limited to, client profile data objects, whole-genome sequence (WGS) data objects, transcriptome data objects, clinical event data objects, risk window prediction data objects, and/or the like, details of which are described herein.

In the present disclosure, the term "client profile data object" refers to a type of data object that represents, indicates, stores and/or comprises data and/or information associated with one or more patients/clients. For example, a client profile data object may be generated by a health care provider or a health insurance provider, and may correspond to or store data/information related to a patient/client. In some embodiments, the client profile data object may comprise data and/or information from electronic medical record(s) (EMR(s)) and/or medical claim(s) associated with the patient.

In some examples, EMRs may represent data and information associated with one or more patients/clients. As an example, EMRs may comprise provider records (such as, but not limited to, notes and information collected by and/or for the clinicians in a doctor's office, a clinic, a pharmacy, a hospital, and/or the like).

In some examples, data and/or information from medical claims may include, but not limited to, medical insurance claims submitted by a patient, a doctor's office, a clinic, a pharmacy, a hospital, and/or the like, which may, for example but not limited to, describe one or more procedures conducted on the patient/client.

While the description above provides examples of data and/or information associated with a client profile data object, it is noted that the scope of the present disclosure is not limited to the description above. In some examples, an example client profile data object may comprise or be associated with one or more additional and/or alternative data/information.

In some embodiments, an example client profile data object may comprise or be associated with one or more whole-genome sequence (WGS) data objects. In the present disclosure, the terms "whole-genome sequence data object" or "WGS data object" refer to a type of data object that represents, indicates, stores and/or comprises data and/or information associated with the entirety, or nearly the entirety, of the deoxyribonucleic acid (DNA) sequence of an organism's genome associated with a patient/client at a single time. For example, an example WGS data object may comprise data and/or information (such as, but not limited to, statistics) related to GWAS as described above.

As an example, an example client profile data object may be associated with a patient/client John, and an example WGS data object associated with the example client profile data object may represent, indicate, store and/or comprise data and/or information associated with the entirety, or nearly the entirety, of the DNA sequence of John's genome.

In some embodiments, an example WGS data object may be associated with a disease identifier. In the present disclosure, the term "disease identifier" refers to an identifier (for example, a name, a code, and/or the like) that uniquely identifies a disease. In some embodiments, a disease identifier may comprise American Standard Code for Information Interchange (ASCII) text, a pointer, a memory address, and the like.

Continuing from the example above, the example WGS data object may be associated with an example disease identifier that indicates type 1 diabetes mellitus (also referred to as "T1D" herein). In such an example, the WGS data object may comprise data and/or information that represents, indicates, stores and/or comprises data and/or information associated with the entirety, or nearly the entirety, of the DNA sequence of genome of an organism and in relationship with T1D.

In some embodiments, an example WGS data object may comprise one or more metadata, such as, but not limited to, one or more PRS metadata and/or one or more PRS-PheWAS metadata. As described above, an example WGS data object may be associated with a disease identifier. As such, an example PRS metadata associated with the example WGS data object may also be associated with the disease identifier, and/or an example PRS-PheWAS metadata associated with the WGS data object may also be associated with the disease identifier.

In the present disclosure, the terms "polygenic risk score metadata" or "PRS metadata" refer to a type of metadata that represents, indicates, stores and/or comprises a PRS based at least in part on and/or derived from a WGS data object. As described above, a PRS metadata may indicate a patient's risk or propensity to a particular disease that may have a significant genetic risk component. As such, the PRS metadata may be associated with a disease identifier, and may indicate a patient's risk or propensity to a disease corresponding to the disease identifier based at least in part on the PRS.

Continuing from the example above, the example WGS data object associated with John may be associated with an example disease identifier that indicates T1D. The example WGS data object may also comprise a PRS metadata. In such an example, the PRS metadata represents, indicates, stores and/or comprises a PRS of T1D for John (e.g. which may indicate the risk or propensity that John may have T1D in his lifetime based at least in part on the PRS).

In the present disclosure, the terms "combined PRS and phenome-wide association study (PRS-PheWAS) metadata" or "PRS-PheWAS metadata" refer to a type of metadata that represents, indicates, stores and/or comprises data/information associated with a combined PRS and phenome-wide association study with respect to a disease based at least in part on or derived from a WGS data object. As such, the PRS-PheWAS metadata may be associated with a disease identifier, and may indicate a patient's risk or propensity to a disease corresponding to the disease identifier based at least in part on the combined PRS and phenome-wide association study. As described, an example method of combined PRS and phenome-wide association study is illustrated in *Association of Polygenic Risk Scores for Multiple Cancers in a Phenome-wide Study: Results from The Michigan Genomics Initiative* by Lars G. Fritsche et al. and published in the AJHG, volume 102, pages 1048-1061, on Jun. 7, 2018, the content of which is incorporated by reference in its entirety. It is noted that the scope of the present disclosure is not limited to this example method only.

For example, a causal linkage to a particular disease may be determined by using the WGS data to conduct a phenome-wide association study (PheWAS) based at least in part on analyzing causal linkage between the patient's index data on the date of PheWAS (e.g. when the sequence was acquired to create the PRS) and then performing a PRS-PheWAS. As described herein, various embodiments of present disclosure may analyze longitudinal clinical data (together with a time-series of differential expression data). In embodiments where the PRS-PheWAS is utilized, such embodiments may provide more accurate predictions in complex conditions (e.g. multiple types of cancer).

Continuing from the example above, the example WGS data object associated with John may be associated with an example disease identifier that indicates T1D. The example WGS data object may also comprise a PRS-PheWAS metadata. In such an example, the PRS-PheWAS metadata represents, indicates, stores and/or comprises a combined PRS and phenome-wide association study of T1D for John (e.g. which may indicate the risk or propensity that John may have T1D in his lifetime based at least in part on the combined PRS and phenome-wide association study).

In some embodiments, an example client profile data object may comprise or be associated with one or more transcriptome data objects. In the present disclosure, the terms "transcriptome data object, "whole-transcriptome data object", and "WT data object" refer to a type of data object that represents, indicates, stores and/or comprises data and/or information associated with the entire set, or nearly the entire set, of the ribonucleic acid (RNA) sequence (including coding and/or non-coding) associated with a patient/client (for example, one or more tissues and/or cells of the patient/client) at a single time.

Continuing from the example above, the example client profile data object may be associated with a patient/client John, and an example transcriptome data object associated with the example client profile data object may represent, indicate, store and/or comprise data and/or information associated with the entire set, or nearly the entire set, of the RNA sequence of one or more tissues and/or cells of John.

In some embodiments, an example transcriptome data object may be associated with a disease identifier. Continuing from the example above, the example transcriptome data object may be associated with an example disease identifier that indicates T1D. In such an example, the transcriptome data object may represent, indicate, store and/or comprise data and/or information associated with the entire set, or nearly the entire set, of the RNA sequence of one or more cells of John that is related to T1D.

In some embodiments, an example transcriptome data object may comprise one or more metadata, such as, but not limited to, one or more tissue-relevant transcriptome metadata and/or one or more scRNA-seq assay metadata. As described above, an example transcriptome data object may be associated with a disease identifier. As such, an example tissue-relevant transcriptome metadata associated with the example transcriptome data object may also be associated with the disease identifier, and/or an example scRNA-seq assay metadata associated with the transcriptome data object may also be associated with the disease identifier.

In the present disclosure, the term "tissue-relevant transcriptome metadata" refer to a type of metadata that represents, indicates, stores and/or comprises data/information in a transcriptome data object that is relevant to one or more particular type of tissues and/or one or more particular types of cells.

For example, an example tissue-relevant transcriptome metadata may be associated with a disease identifier, which indicates that the example tissue-relevant transcriptome metadata represents, indicates, stores and/or comprises data/information in a transcriptome data object related to one or more particular tissues or one or more particular cells that are relevant to the disease indicated by the disease identifier.

In some embodiments, an example tissue-relevant transcriptome metadata may be based at least in part on or derived from an example single-cell ribonucleic acid (RNA) sequencing assay metadata. In the present disclosure, the terms "single-cell ribonucleic acid sequencing assay metadata" or "scRNA-seq assay metadata" refer to a type of metadata that represents, indicates, stores and/or comprises data/information in a transcriptome data object that is relevant to a single-cell RNA sequencing assay. An example method of single-cell RNA sequencing assay is illustrated in *A practical guide to single-cell RNA-sequencing for biomedical research and clinical applications* by Ashraful Haque et al. and published in Genome Medicine, volume 9, article number 17, in 2017, the content of which is incorporated by reference in its entirety. It is noted that the scope of the present disclosure is not limited to this example method only.

For example, an example scRNA-seq assay metadata may be associated with a disease identifier, which indicates that the example scRNA-seq assay metadata represents, indicates, stores and/or comprises data/information in a transcriptome data object related to a single-cell RNA sequencing assay that is relevant to the disease indicated by the disease identifier.

In the present disclosure, the term "differential expression metadata" refers to a type of metadata that represents, indicates, stores and/or comprises data/information associated with difference(s) of gene expressions between two or more transcriptome data objects, between two or more tissue-relevant transcriptome metadata, and/or between two or more scRNA-seq assay metadata. Examples of calculating differential expression metadata is described herein.

In the present disclosure, the term "clinical event data object" refers to a type of data object that represents, indicates, stores and/or comprises data and/or information associated with one or more clinical events associated with a patient/client. For example, an example clinical event data object may comprise data and/or information associated with one or more visits conducted by a patient/client to a doctor's office, a clinic, a pharmacy, a hospital, and/or the like to seek medical help, medical treatment, medical assistance, pharmacy prescriptions, and/or the like.

In some embodiments, an example clinical event data object may comprise symptom metadata. In the present disclosure, the term "symptom metadata" refer to a type of metadata that represents, indicates, stores and/or comprises data and/or information associated with one or more symptoms that is related to a disease (for example, medical symptoms such as, but not limited to, stomach cramps, throbbing headache, fatigue, and/or the like) and experienced by a patient/client.

In some embodiments, example clinical event data objects, example WGS data objects, and/or example transcriptome data objects may be associated with example temporal identifiers. In the present disclosure, the term "temporal identifier" refers to an identifier that may be in the form of a time code or a time stamp that identifies the date and/or time associated with an example WGS data object and/or an example transcriptome data object (for example, an example tissue-relevant transcriptome metadata, an example scRNA-seq assay metadata).

As described above, an example WGS data object may comprise data and/or information of DNA sequence associated with a patient/client. In some embodiments, if a WGS data object is associated with a temporal identifier indicating a date and/or time, it indicates that the DNA is collected or sampled on that date and/or time, the DNA is sequenced on that date and/or time, and/or the WGS data object is generated on that date and/or time.

As an example, if an example WGS data object is associated with a temporal identifier of Jan. 1, 2021, it may indicate that data and/or information of the WGS data object is based at least in part on DNA collected or sampled from the patient/client on Jan. 1, 2021. For example, as described above, an example WGS data object may comprise PRS metadata. In this example, the PRS of the PRS metadata may be calculated based at least in part on the DNA collected or sampled from the patient/client on Jan. 1, 2021.

As described above, an example transcriptome data object may comprise data and/or information of RNA sequence associated with a patient/client. In some embodiments, if a transcriptome data object is associated with a temporal identifier indicating a date and/or time, it indicates that the RNA is collected or sampled on that date and/or time, the RNA is sequenced on that date and/or time, and/or the transcriptome data object is generated on that date and/or time.

As an example, if an example transcriptome data object is associated with a temporal identifier of Jan. 1, 2021, it may indicate that data and/or information of the transcriptome data object is based at least in part on RNA collected or sampled from the patient/client on Jan. 1, 2021. For example, as described above, an example transcriptome data object may comprise scRNA-seq assay metadata. In this example, the scRNA-seq assay metadata may be calculated based at least in part on the RNA collected or sampled from the patient/client on Jan. 1, 2021.

As described above, an example clinical event data object may be associated with one or more visits conducted by a patient, and may comprise symptom metadata describing one or more symptoms associated with a patient/client. In some embodiments, if the example clinical event data object is associated with a temporal identifier indicating a date and/or time, it indicates that the symptom occurred on the date and/or time indicated by the temporal identifier, and/or that the visit was conducted on the date and/or time indicated by the temporal identifier.

For example, if an example clinical event data object is associated with a temporal identifier of Jan. 1, 2021, it may indicate that data and/or information of the clinical event data object is based at least in part on a visit by the patient/client on Jan. 1, 2021, and/or that the symptoms described in the symptom metadata associated with the example clinical event data object occurred on Jan. 1, 2021.

In the present disclosure, the term "dynamic multigraph data object" refers to a data object that is in the form of a data graph and comprises one or more dynamically generated nodes representing a stream of timed events and/or one or more dynamically generated edges that connect nodes. In some embodiments, an example dynamic multigraph data object may be generated based at least in part on at least one initial transcriptome data object, at least one subsequent transcriptome data object, and at least one clinical event data object, details of which are described herein.

In the present disclosure, the term "machine learning model" refers to a software computer program (and, in some embodiments, associated hardware) that is trained to process, analyze, generate, integrate, summarize, translate, and/or predict one or more output datasets based at least in part on one or more input datasets. For example, an example machine learning model may be trained to recognize patterns in the one or more input datasets, identify trends from the one or more input datasets, generate one or more predictions based at least in part on the one or more input datasets, and/or the like.

In the present disclosure, the terms "temporal graph network" or "TGN" refer to a type of machine learning model that comprises an encoder architecture that learns on dynamic graphs representing a stream of events and generates one or more predictions based at least in part on the stream of events. For example, an example TGN may create compressed representations of nodes in the dynamic graphs based at least in part on their interactions, and, upon detecting each event, update them accordingly. In some example, an example TGN may comprise a memory module for storing the state of nodes, a message function module and a message updater module for updating the memory component, a message aggregator module for aggregating messages associated with the events, and an embedding module for generating temporal embeddings of nodes. In some embodiments, an example TGN is trained based at least in part on dynamic multigraph data objects and generates risk window prediction data objects, details of which are described herein.

In the present disclosure, the term "risk window prediction data object" refers to a type of data object that represents, indicates, stores and/or comprises data and/or information associated with a predicted time frame of a disease that will be or has been onset in a patient/client. In the present disclosure, a disease is considered to be "onset" in a patient/client when the disease is fully symptomatic in the patient/client.

In some embodiments, an example risk window prediction data object may comprise an estimated lower bound metadata and an estimated upper bound metadata. In the present disclosure, the term "estimated lower bound metadata" refers to a type of metadata that represents, indicates, stores and/or comprises a time code or a time stamp that indicates the earliest date and/or time that a disease is estimated to be onset in a patient/client based at least in part on the risk window prediction data object. In the present disclosure, the term "estimated upper bound metadata" refers to a type of metadata that represents, indicates, stores and/or comprises a time code or a time stamp that indicates the latest date and/or time that a disease is estimated to be onset in a patient/client based at least in part on the risk window prediction data object.

In some embodiments, a validated onset temporal metadata may be associated with a client profile data object. In the present disclosure, the term "validated onset temporal metadata" refers to a type of metadata that represents, indicates, stores and/or comprises a time code or a time stamp that indicates a clinically validated date and/or time that a disease is onset in a patient/client.

In the present disclosure, the term "data operation" refers to a computer operation associated with a data element or a data object. Examples of data operations may include, but not limited to, transmitting one or more data objects from one device to another device, rendering one or more data objects on a user interface that is displayed on a display device, and/or the like.

c. Exemplary Generation of Risk Window Prediction Data Object

As described above, there are technical challenges, deficiencies and problems associated with machine learning systems and methods, and various example embodiments of the present disclosure overcome such challenges. For example, referring now to FIG. 4, an example method 400 of generating an example risk window prediction data object that overcomes various technical challenges in accordance with embodiments of the present disclosure is illustrated.

Figure 4:
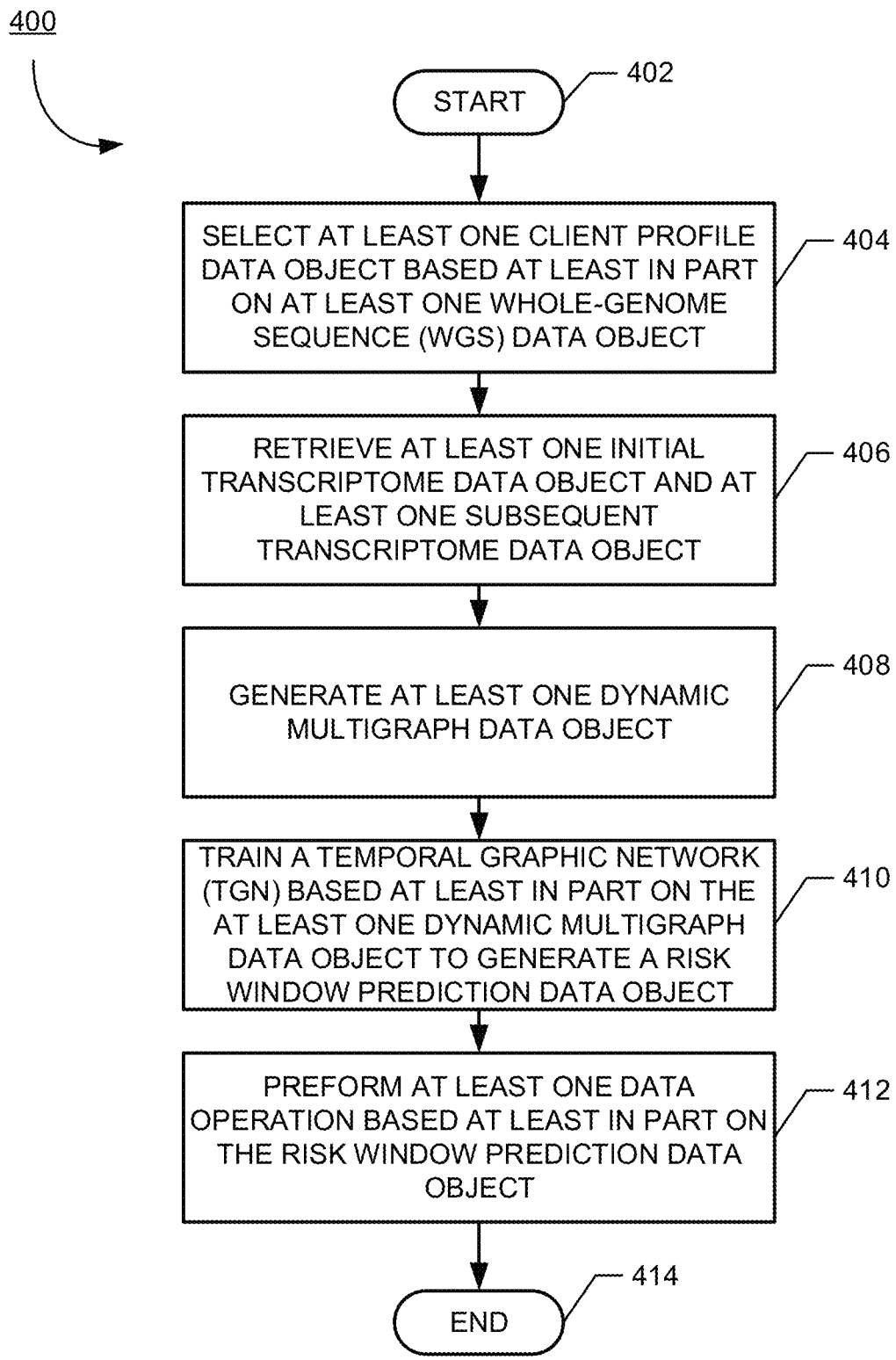

As shown in FIG. 4, the example method 400 starts at step/operation 402. Subsequent to step/operation 402, the example method 400 proceeds to step/operation 404. At step/operation 404, a computing entity (such as the data object computing entity 105 described above in connection with FIG. 1 and FIG. 2) may include means (such as the processing element 205 of the data object computing entity 105 described above in connection with FIG. 2) to select at least one client profile data object based at least in part on at least one WGS data object.

In some embodiments, the processing element may select at least one client profile data object from a plurality of client profile data objects based at least in part on at least one WGS data object related to a disease identifier and associated with the at least one client profile data object.

In some embodiments, the at least one WGS data object comprises at least one of at least one PRS metadata related to the disease identifier or at least one PRS-PheWAS metadata related to the disease identifier. In some embodiments, the processing element may select at least one client profile data object from a plurality of client profile data objects based at least in part on the PRS metadata associated with the at least one client profile data object and related to the disease identifier. In some embodiments, the processing element may select at least one client profile data object from a plurality of client profile data objects based at least in part on the PRS-PheWAS metadata associated with the at least one client profile data object and related to the disease identifier For example, the processing element may select at least one client profile data object from a plurality of client profile data objects associated with patient/client Adam, patient/client Brandon, and patient/client Cindy. As an example, the processing element may select a disease identifier that corresponds to non-small cell lung cancer (NSCLC). The processing element may retrieve a WGS data object associated with the client profile data object associated with Adam, and the WGS data object may comprise a PRS metadata and/or a PRS-PheWAS metadata associated with the disease identifier that corresponds to NSCLC. In such an example, the PRS metadata and/or the PRS-PheWAS metadata may indicate a risk or propensity that Adam will have NSCLC in his lifetime based at least in part on Adam's DNA sequence data from the WGS data object. The processing element may determine whether the PRS metadata and/or the PRS-PheWAS metadata satisfies a threshold, and, if so, select the client profile data object associated with Adam. Similarly, the processing element may retrieve a WGS data object associated with the client profile data object associated with Brandon, and the WGS data object may comprise a PRS metadata and/or a PRS-PheWAS metadata associated with the disease identifier that corresponds to NSCLC. In such an example, the PRS metadata and/or the PRS-PheWAS metadata may indicate a risk or propensity that Brandon will have NSCLC in his lifetime based at least in part on Brandon's DNA sequence data from the WGS data object. The processing element may determine whether the PRS metadata and/or the PRS-PheWAS metadata satisfies a threshold, and, if so, select the client profile data object. Similarly, the processing element may determine whether to select the client profile data object associated with Cindy based at least in part on the WGS data object, the PRS metadata and/or the PRS-PheWAS metadata associated with Cindy's client profile data object.

While the description above provides an example of selecting at least one client profile, it is noted that the scope of the present disclosure is not limited to the description above. For example, additional details associated with selecting at least one client profile data object are described herein, including, but not limited to, those in connection with at least FIG. 6.

Referring back to FIG. 4, subsequent to step/operation 404, the example method 400 proceeds to step/operation 406. At step/operation 406, a computing entity (such as the data object computing entity 105 described above in connection with FIG. 1 and FIG. 2) may include means (such as the processing element 205 of the data object computing entity 105 described above in connection with FIG. 2) to retrieve at least one initial transcriptome data object and at least one subsequent transcriptome data object.

In some embodiments, the processing element may retrieve at least one initial transcriptome data object and at least one subsequent transcriptome data object related to the disease identifier and associated with the at least one client profile data object selected at step/operation 404.

As described above, an example transcriptome data object may represent, indicate, store and/or comprise data and/or information associated with the entire set, or nearly the entire set, of RNA sequence associated with a patient/client. For example, the example transcriptome data object may comprise tissue-relevant transcriptome metadata associated with the RNA sequence that is relevant to one or more particular tissues or one or more particular cells associated a disease indicated by a disease identifier. Additionally, or alternatively, the example transcriptome data object may comprise scRNA-seq assay metadata associated with a single-cell RNA sequencing assay that is related to a particular type of cell or tissue associated with a disease indicated by the disease identifier.

In some embodiments, a subsequent transcriptome data object is generated based at least in part on RNA sequence that is collected and/or sampled subsequent to an initial transcriptome data object. For example, the initial transcriptome data object may comprise an initial tissue-relevant transcriptome metadata associated with the disease identifier, and the at least one subsequent transcriptome data object may comprise a subsequent tissue-relevant transcriptome metadata associated with the same disease identifier. In this example, the subsequent tissue-relevant transcriptome metadata is generated based at least in part on RNA sequence that is collected and/or sampled subsequent to that of the initial tissue-relevant transcriptome metadata. Additionally, or alternatively, the initial transcriptome data object may comprise an initial scRNA-seq assay metadata associated with the disease identifier, and the at least one subsequent transcriptome data object may comprise a subsequent scRNA-seq assay metadata associated with the same disease identifier. In this example, the subsequent scRNA-seq assay metadata is generated based at least in part on RNA sequence that is collected and/or sampled subsequent to that of the initial scRNA-seq assay metadata.

In some embodiments, the at least one subsequent transcriptome data object is associated with at least one clinical event data object. As described above, a clinical event data object may comprise data and/or information associated with a visit conducted by a patient/client to a doctor's office. In some embodiments, a subsequent transcriptome data object is associated with a clinical event data object when the RNA sequence associated with the subsequent transcriptome data object is collected and/or sampled during a visit represented by the clinical event data object. As described above, a subsequent transcriptome data object may be associated with a disease identifier. As such, in some embodiments, the symptom metadata of the clinical event data object may indicate one or more symptoms that are also associated with the disease identifier.

Continuing from the example above, assuming that the client profile data object associated with Adam is selected at step/operation 404, the processing element may proceed to retrieving at least one initial transcriptome data object associated with Adam and related to NSCLC and at least one subsequent transcriptome data object associated with Adam and related to NSCLC at step/operation 406. For example, on the same day that Adam's DNA is collected and/or sampled to generate the WGS data object related to NSCLC, Adam's RNA is also collected and/or sampled to generate an initial transcriptome data object related to NSCLC. Adam may conduct subsequent visits to the doctor's office. For example, Adam may conduct a subsequent visit to a doctor's office and describe symptoms related to NSCLC (for example, but not limited to, cough, chest pain, and/or the like). In this example, a clinical event data object is generated and comprises symptom metadata associated with NSCLC, and Adam's RNA is collected or sampled during the visit to conduct a scRNA-seq assay (for example, based at least in part on the RNA of Adam's lung tissue). A transcriptome data object is generated based at least in part on the scRNA-seq assay (for example, the transcriptome data object may comprise scRNA-seq assay metadata based at least in part on the scRNA-seq assay), and the transcriptome data object is associated with the clinical event data object.

While the description above provides an example of collecting/sampling RNA of one type of cell or tissue in generating a transcriptome data object, it is noted that the scope of the present disclosure is not limited to the description above. In some examples, the RNAs of more than one type of cells or tissues may be collected and/or sampled (during, for example, a visit to the doctor's office), such as, but not limited to, cellular components of the adaptive immune system in the case of autoimmune disease. Additionally, or alternatively, various examples of the present disclosure may extend to multiple scRNA collections for different disease types that are involved in a specific disease in question. As an example, cardiac scRNA assaying may be relevant to renal disease, so both cardiac scRNA assay and kidney scRNA assay are performed when the patient is exhibiting symptoms related to renal disease (for example, during a visit to the doctor's office).

Referring back to FIG. 4, subsequent to step/operation 406, the example method 400 proceeds to step/operation 408. At step/operation 408, a computing entity (such as the data object computing entity 105 described above in connection with FIG. 1 and FIG. 2) may include means (such as the processing element 205 of the data object computing entity 105 described above in connection with FIG. 2) to generate at least one dynamic multigraph data object.

In some embodiments, the processing element may generate at least one dynamic multigraph data object based at least in part on the at least one initial transcriptome data object retrieved at step/operation 406, the at least one subsequent transcriptome data object retrieved at step/operation 406, and the at least one clinical event data object associated with the at least one subsequent transcriptome data object retrieved at step/operation 406.

As described above, the at least one initial transcriptome data object, the at least one subsequent transcriptome data object, and the at least one clinical event data object may each be associated with at least one temporal identifier. In some embodiments, the dynamic multigraph data object may comprise a plurality of nodes connected in a time axis, each corresponding to a temporal identifier associated with one of the at least one initial transcriptome data object, the at least one subsequent transcriptome data object, and/or the at least one clinical event data object. In some embodiments, each of the plurality of nodes may be connected to a graphic representation of the corresponding at least one initial transcriptome data object, the corresponding at least one subsequent transcriptome data object, and/or the corresponding at least one clinical event data object. Examples of dynamic multigraph data objects are illustrated and described in connection with at least FIG. 8, FIG. 10, and FIG. 12 herein.

Referring back to FIG. 4, subsequent to step/operation 408, the example method 400 proceeds to step/operation 410. At step/operation 410, a computing entity (such as the data object computing entity 105 described above in connection with FIG. 1 and FIG. 2) may include means (such as the processing element 205 of the data object computing entity 105 described above in connection with FIG. 2) to train a TGN based at least in part on the at least one dynamic multigraph data object to generate a risk window prediction data object associated with the disease identifier.

As described above, the risk window prediction data object refers to a type of data object that represents, indicates, stores and/or comprises data and/or information associated with a predicted time frame of a disease that will be or has been onset in a patient/client. In some embodiments, the processing element may provide the at least one dynamic multigraph data object as an input dataset to a TGN for training, and the TGN may generate a risk window prediction data object as an output dataset. In some embodiments, the processing element may retrieve a validated onset temporal metadata associated with the at least one dynamic multigraph data object and cause the TGN to update one or more of its parameters so that the risk window prediction data object corresponds to the validated onset temporal metadata (e.g. the date and/or time indicated by the validated onset temporal metadata falls within the predicted time frame indicated by the risk window prediction data object). As such, the processing element may improve the precision and accuracy of risk window prediction data objects generated by the TGN. Additional details are described herein.

Additionally, or alternatively, the processing element may provide the at least one dynamic multigraph data object to a TGN that has been trained, and the TGN may generate a risk window prediction data object corresponding to the at least one dynamic multigraph data object. Additional details are described herein.

While the description above provides an example of implementing TGN as a machine learning model for generating the risk window prediction data object, it is noted that the scope of the present disclosure is not limited to the description above. In some examples, an example method may implement one or more additional or alternative machine learning methods.

Referring back to FIG. 4, subsequent to step/operation 410, the example method 400 proceeds to step/operation 412. At step/operation 412, a computing entity (such as the data object computing entity 105 described above in connection with FIG. 1 and FIG. 2) may include means (such as the processing element 205 of the data object computing entity 105 described above in connection with FIG. 2) to perform at least one data operation based at least in part on the risk window prediction data object.

In some embodiments, the processing element may transmit the risk window prediction data object to a client computing entity. In some embodiments, the processing element may render the risk window prediction data object on a user interface that is on a display of the client computing entity. Additionally, or alternatively, the processing element may perform one or more other data operations based at least in part on the risk window prediction data object generated at step/operation 410.

Referring back to FIG. 4, subsequent to step/operation 412, the example method 400 proceeds to step/operation 414 and ends.

Figure 5:
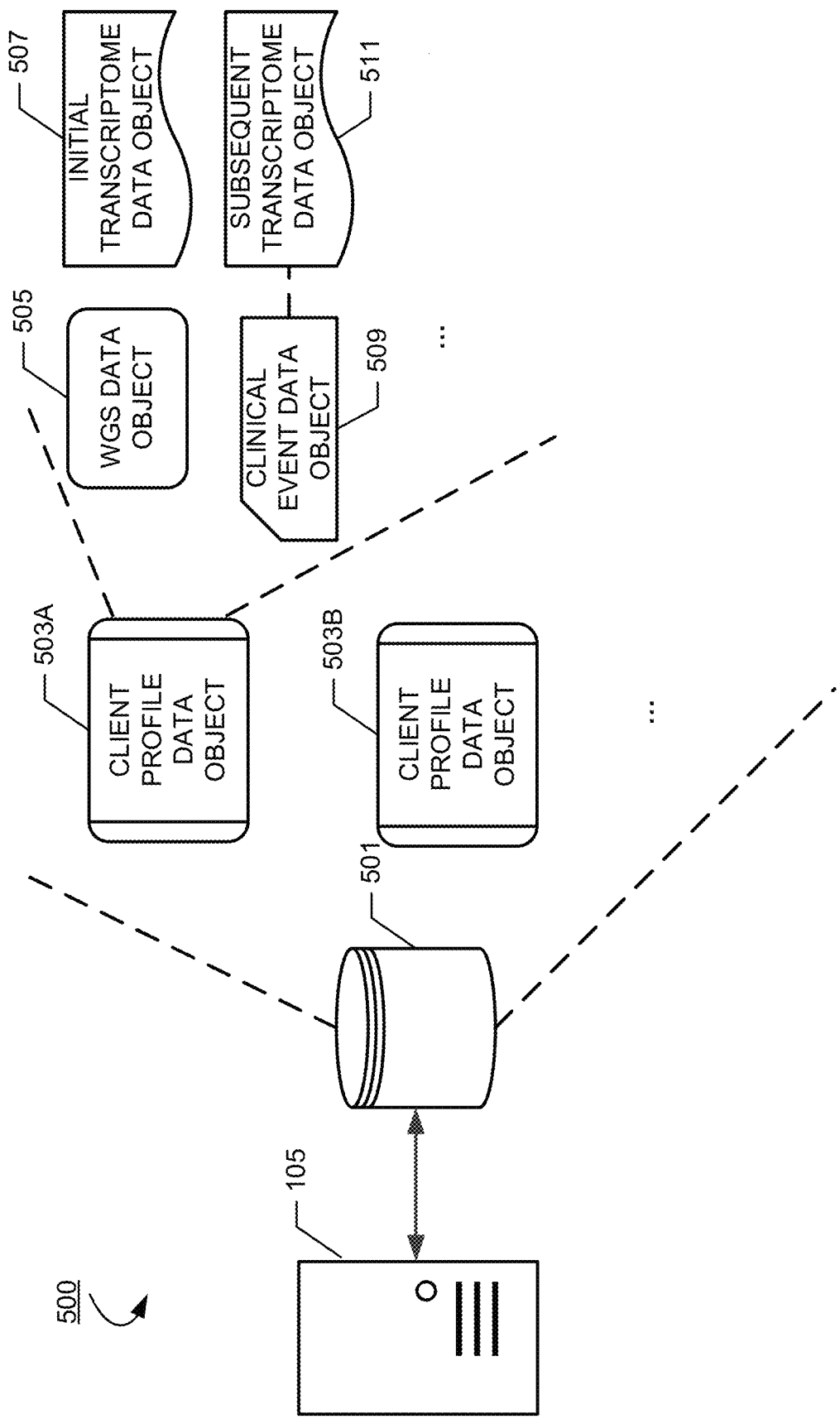

Referring now to FIG. 5, an example diagram 500 is illustrated. In particular, the example diagram 500 illustrates example data communications between the data object computing entity 105 and a database 501 that may store data objects such as, but not limited to, client profile data objects (such as, but not limited to, client profile data object 503A and client profile data object 503B), WGS data objects (such as, but not limited to, WGS data object 505), clinical event data objects (such as, but not limited to, clinical event data object 509), initial transcriptome data objects (such as, but not limited to, initial transcriptome data object 507), and subsequent transcriptome data objects (such as, but not limited to, subsequent transcriptome data object 511).

In some embodiments, each of the client profile data objects stored in the database 501 may be associated with a corresponding client identifier that uniquely identifies a client profile data object associated with a patient/client, and the processing element may retrieve one or more client profile data objects based at least in part on the corresponding client identifier(s).

In some embodiments, a client profile data object may be associated with one or more WGS data objects, one or more clinical event data objects, and/or one or more transcriptome data objects. In the example shown in FIG. 5, the client profile data object 503A is associated with at least the WGS data object 505, the initial transcriptome data object 507, the subsequent transcriptome data object 511, and the clinical event data object 509.

In some embodiments, a transcriptome data object is associated with one or more clinical event data objects. In the example shown in FIG. 5, the subsequent transcriptome data object 511 is associated with the clinical event data object 509, which may indicate that the subsequent transcriptome data object 511 and the clinical event data object 509 are associated with the same temporal identifier. For example, the subsequent transcriptome data object 511 is generated based on RNA sequenced or sampled from a patient/client during a doctor's visit corresponding to the clinical event data object 509.

Various embodiments of the present disclosure may utilize the integration of one or more WGS data objects (in the form of either a PRS metadata or a PRS-PheWAS metadata), one or more transcriptome data objects (and further specific scRNA-seq assay metadata that may comprise periodic analysis of differential gene expression assays) to determine patterns of disease-relevant tissue differential expression, together with other data and/or information associated with client profile data object (such as, but not limited to, clinical event data objects from EMR data and claims data), to triangulate and determine the most likely onset window of a specific patient's disease or to reduce uncertainty in the time frame for disease onset.

In some embodiments, an example method relies upon three distinct datasets, and uses these datasets in a framework similar to coordinate triangulation or trilateration. For example, various embodiments of the present disclosure may use evolving data from:

(1) a WGS data object (for example, the WGS data object 505 shown in FIG. 5) associated with the patient (for example, associated with the client profile data object 503A). Example methods of the present disclosure may derive a PRS (and/or possibly a PRS-PheWAS) from the WGS data object. In some embodiments, the PRS may establish a baseline genetic risk. For example, an example PRS may be determined based on LDpred, which a Bayesian PRS that estimates posterior mean causal effect sizes from the WGS data object. An example of LDpred is described in *Modeling Linkage Disequilibrium Increases Accuracy of Polygenic Risk Scores* by Bjarni J. Vilhjalmsson et al. and published in the AJHG, volume 97, issue 4, pages 576-592, Oct. 1, 2015, the content of which is incorporated by reference in its entirety.

(2) one or more transcriptome data objects (for example, the initial transcriptome data object 507 and the subsequent transcriptome data object 511) associated with a patent (for example, associated with the client profile data object 503A), such as the patient's tissue-relevant transcriptome metadata, acquired via scRNA-seq during key clinical events. Examples of key clinical events include, but not limited to, a baseline date (e.g. index date at which the corresponding WGS was acquired), one or more major clinical events (e.g. acute renal failure, then at hospitalization due to suspected myocardial infarction (MI), etc.). In some embodiments, the one or more transcriptome data objects may produce molecular "fingerprints" of disease progression.

(3) one or more clinical event data objects (for example, the clinical event data object 509 based at least in part on the longitudinal EMR and/or claims data) with an index date of each scRNA-seq study. As such, a time series of differential expression for the tissue(s) relating to the corresponding clinical events are obtained. In some embodiments, such a time series may be irregular in nature as each scRNA-seq assay is tied to a clinical event.

While the description above provides example sources of data in accordance with examples of the present disclosure, it is noted that the scope of the present disclosure is not limited to the description above. In some examples, an example embodiment may comprise one or more additional and/or alternative elements.

For example, epigenetic data objects associated with the client profile data objects may additionally, or alternatively, be utilized to generate a dynamic multigraph data object and/or a risk window prediction data object. In the more general case, epigenomic data objects may be acquired and generated at each clinical event for each patient. The epigenomic data objects may comprise and/or represent epigenetic data and/or epigenomics data associated with the patient. The dynamic multigraph data object may be extended to account for epigenomic data objects, which may be applied to a TGN as described herein. Various examples described herein refer to scRNA-seq data and may assume that the resultant differential expression is causal, to leading-order, in the context of "risk window" estimation. In other words, epitranscriptome models are considered to modify expression and thus, by measuring differential expression, various embodiments of the present disclosure approximately capture the principal effector on the "risk window." In some embodiments, epigenomics data may refine the "risk window" prediction accuracy, at additional financial cost of sequencing and additional complexity in the structure of the dynamic multigraph data object. As such, for simplicity, various embodiments of the present disclosure may rely on tissue transcriptome and differential expression data.

As such, various embodiments of the present disclosure may provide a multi-omics framework that may predict a risk window for the full symptomatic onset of a given genetic 38 LEGAL02/40684941v7 disease. For example, various embodiments of the present disclosure may leverage epigenetic data that suggests that the development of a given genetic disease involves epigenomic changes over time, or an epigenomic trajectory. As such, various embodiments of the present disclosure involve genome sequencing of a cohort of patients susceptible to a given disease at multiple points in time. Various embodiments of the present disclosure may additionally implement dynamic multigraph data objects, and train machine learning networks on the dynamic multigraph data objects to generate a risk window prediction data object. One of the many technical benefits of the present discourse is providing a risk window prediction data object that predicts a temporal window within which the given disease may become fully symptomatic.

According to various embodiments of the present disclosure, the following operations are performed: identifying a cohort of individuals at risk for a genetic disease based at least in part on PRS metadata for each individual; receiving baseline genetic sequencing data for each individual in the identified cohort of individuals; receiving subsequent genetic sequencing data for the identified cohort of individuals, where the subsequent genetic sequencing data are associated with points in time when significant health events are experienced by the plurality of individuals; generating a dynamic multigraph data object based at least in part on the baseline and subsequent genetic sequencing data for the cohort of individuals; and predicting a risk window for the most likely symptomatic onset time period for the genetic disease based at least in part on the dynamic multigraph data object.

In some embodiments, identifying a specific genetic disease and individuals susceptible to developing the specific disease may be based at least in part on PRSs. In particular, genetic diseases associated with multiple causal genetic variants, such as T1D, may be identified or selected. A cohort of interest composed of a plurality of individuals may be identified, where each individual may have a threshold-satisfying risk score for the given genetic disease. Risk scoring may be in the form of generating PRSs or risk scoring via a PRS-PheWAS. Generating PRSs may be performed using various techniques such as LDpred. Risk scoring each individual in the cohort may also involve recording an index date at which risk scoring was performed. This initial risk scoring date provides a starting, or baseline, date with reference to which a disease timeline/trajectory may be generated. Additional analysis and selection of the cohort may be performed to ensure sufficient subject numbers and determine whether comprehensive EMR data for each individual exists.

For each individual in the cohort of interest, baseline genetic sequencing may be performed (for example, to generate an initial transcriptome data object). Because various embodiments of the present disclosure leverage the epigenetic evolution in disease progression, baseline genetic sequencing data may be important as a reference to observe temporal changes in subsequent genetic sequencing data. Baseline genetic sequencing may be performed at substantially the same time as the risk scoring, or on the initial risk scoring date. Genetic sequencing may involve a single-cell RNA sequencing assay of the tissue associated with the given genetic disease (e.g., lung tissue when the given genetic disease is NSCLC).

Following the baseline genetic sequencing, various significant health events associated with the given genetic disease may be identified or determined. For example, an episode of dysglycaemia may be determined to be a significant health event when the given genetic disease is T1D, due to the 75% risk of T1D occurrence following a dysglycaemia episode. In other words, significant health events may be determined based at least in part on events associated with an increased risk of the development or onset of the given genetic disease.

With significant health events being determined, each individual of the cohort may be tracked or monitored, such that should an individual experience a significant health event, subsequent genetic sequencing is performed for the individual at that point in time. As such, subsequent genetic sequencing data may be collected and associated with points in time when significant health events are experienced. Occurrence likelihood data may also be stored or associated with the subsequent genetic sequencing data (e.g., 75% increased risk after dysglycaemia for T1D).

Thus, as a result, subsequent genetic sequencing may comprise generating multiple genetic sequencing data (e.g. subsequent transcriptome data objects) for each significant health event (e.g. associated with clinical event data objects) experienced by each individual in the cohort. Meanwhile, fully symptomatic onset of the given genetic disease for a specific individual is also noted as a significant health event, at which point endpoint genetic sequencing is performed and monitoring is not continued for the specific individual.

Using the baseline and subsequent genetic sequencing data for each individual in the cohort, a dynamic multigraph data object may be generated. Temporal identifiers related to when significant health events are experienced and subsequent genetic sequencing data are collected are indicated on each timeline. Additionally, timelines/trajectories for each individual span from the initial risk scoring date to the time of fully symptomatic onset of the given genetic disease. Various embodiments of the present disclosure may further utilize data from electronic medical records (EMRs) and claims data.

Various embodiments of the present disclosure may train a machine learning network on the generated dynamic multigraph data object. Specifically, a TGN, which is a type of graph machine learning model, may be trained on the dynamic multigraph data object. The TGN may identify differential genetic expression states between points in time when significant health events are experienced. In other words, genetic sequencing data at different points in time may be compared, thereby deriving a temporal evolution of genetic expression in disease tissue.

Following training of the TGN, the TGN may predict a risk window for symptomatic onset of the given disease. The risk window may comprise an estimated lower bound metadata and estimated upper bound metadata. A confidence interval associated with the risk window prediction data object may also be generated, as well as estimated probabilities for the estimated lower bound metadata and the estimated upper bound metadata.

As such, the risk window prediction data object provides an estimated time period for disease onset based at least in part on (a) baseline risk scoring, (b) genetic sequencing data across points in time of significant health events, and (c) a temporal trajectory based at least in part on EMR and/or claims data indicating when significant health events have occurred. Risk window prediction data objects may be fed back into the TGN to enable a continuous learning paradigm, thereby refining and improving the accuracy of future predictions generated by the TGN.

b. Exemplary Generation of Dynamic Multigraph Data Object

As described above, graph databases and graph machine learning methods have become an intensive area of research, and there are several areas whereby such knowledge representations can make advances in biology and life science applications. For example, the Optum Healthcare Graph is the largest healthcare database, which illustrates the power that these methods can bring in terms of actionable insights.

However, many graphs are not static. For example, in social media platforms such as Twitter, if a poster with a large number of followers writes a post that generates a lot of comments and, critically, many "re-tweets," then the graph representation of this particular network will evolve over time, with potentially many new edges created. This is an example of a dynamic graph: the temporal evolution of such a system requires specialized analysis methods, as it is the dynamic structure that contains critical insights about the system and how it evolves. Dynamic graphs can be continuous (e.g. graph edges can appear at any time point) and evolving (e.g. new nodes join the graph continuously), and an effective machine learning method must take these considerations into account.

In accordance with various embodiments of the present disclosure, dynamic multigraph data objects may be in the form of continuous-time dynamic graphs (CTDGs) that can be represented as timed lists of events, which may include edge addition or deletion, node addition or deletion, and node or edge feature transformations. In some embodiments, CTDGs provide ideal framework for analysis of the data because the association of longitudinal clinical events with differential expression data from a "base date" of a PRS can be represented and analyzed in the same framework (even though, in some embodiments, there will only be addition of nodes and not node deletions).

Figure 6:
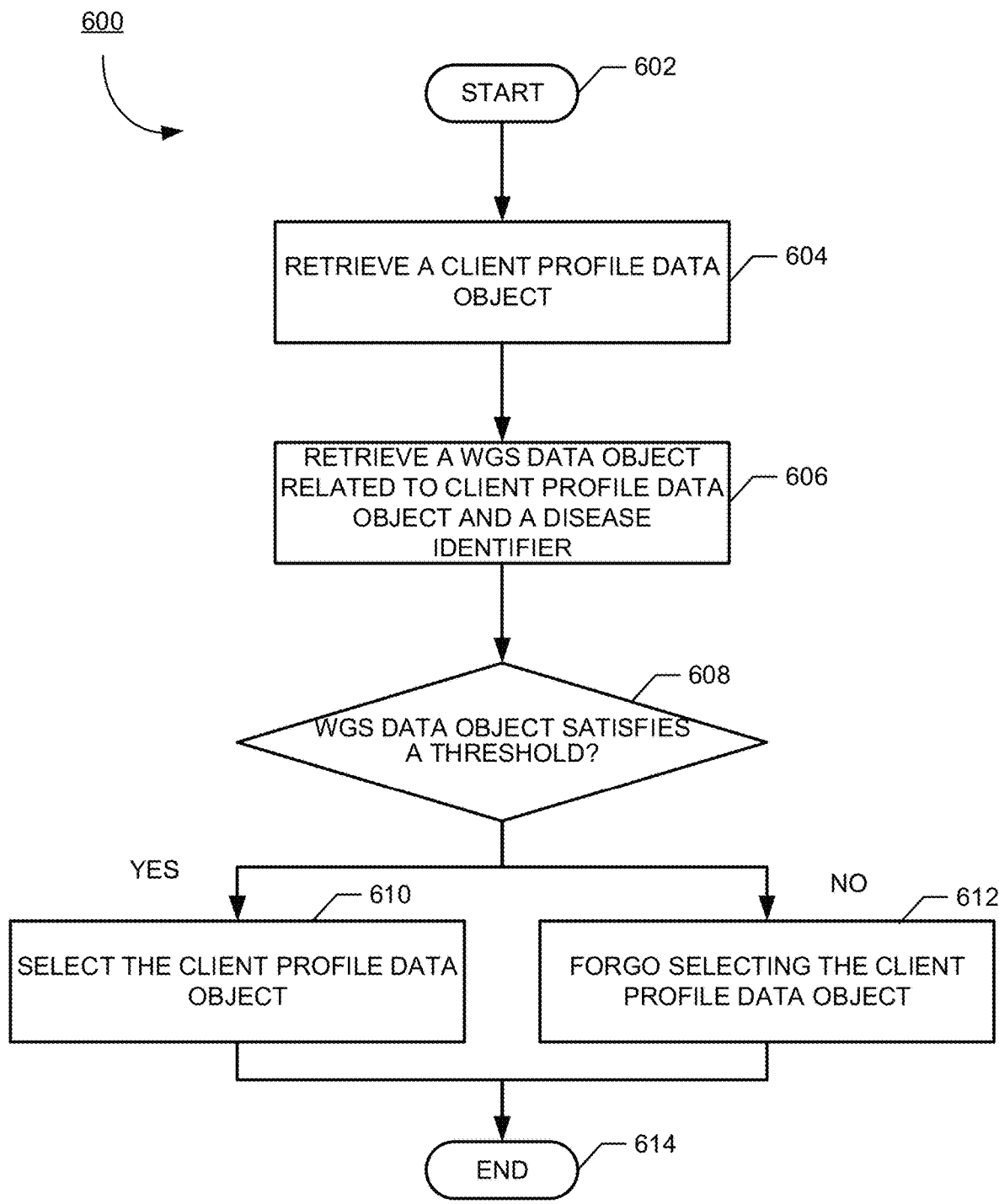
Figure 7:
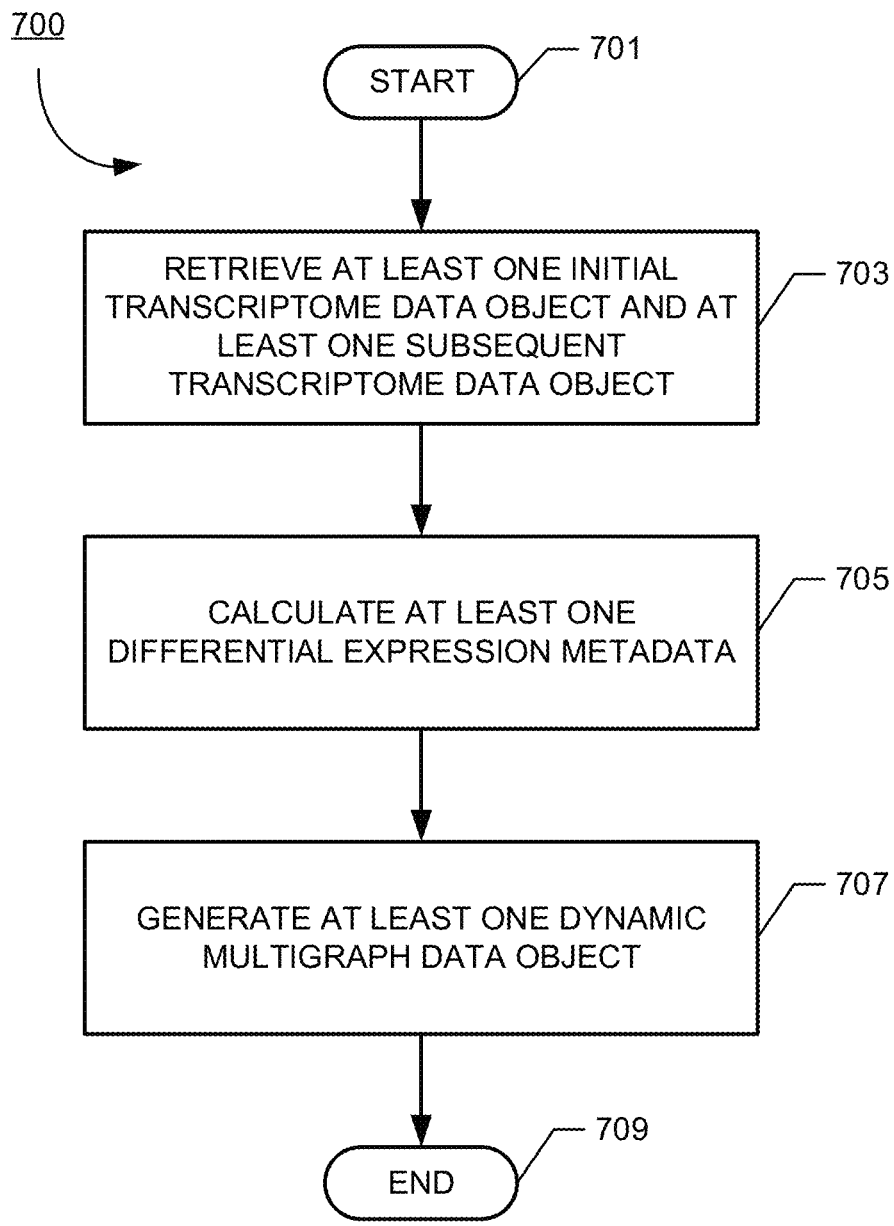
Figure 8:
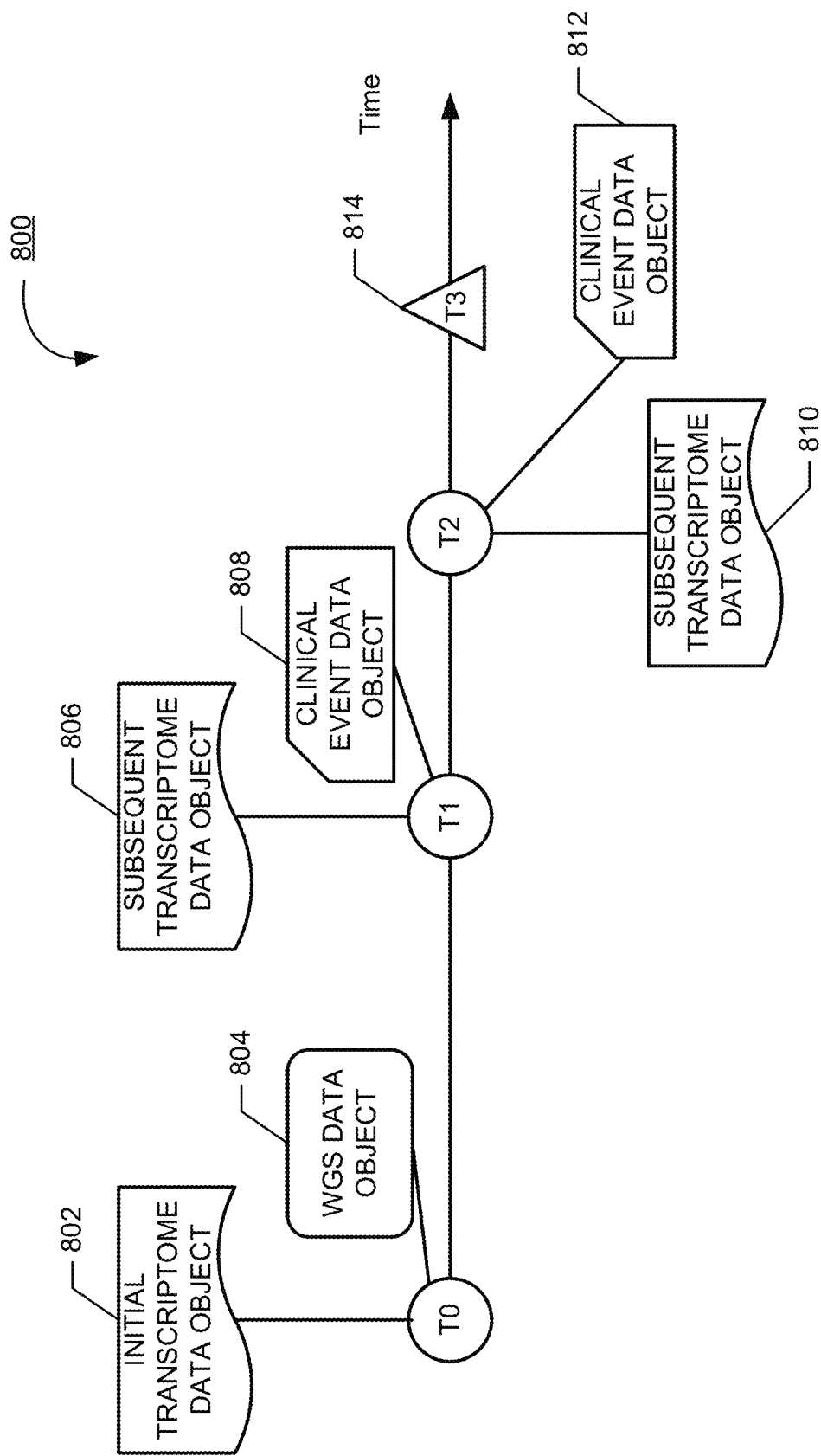

In various embodiments of the present disclosure, a computing entity (such as the data object computing entity 105 described above in connection with FIG. 1 and FIG. 2) may implement various processing techniques (including, but not limited to, one or more encoding and/or embedding techniques) to generate at least one dynamic multigraph data object (for example, in connection with step/operation 408 of FIG. 4 described above). Referring now to FIG. 6-FIG. 8, various examples associated with generating dynamic multigraph data objects are illustrated.

Referring now to FIG. 6, an example method 600 illustrates an example of selecting client profile data object in accordance with embodiments of the present disclosure. In particular, the example method 600 illustrates an example of selecting client profile data objects associated with only clients/patients whose risk level of a particular disease satisfies one or more thresholds for generating the dynamic multigraph data object.

As shown in FIG. 6, the example method 600 starts at step/operation 602. Subsequent to step/operation 602, the example method 600 proceeds to step/operation 604. At step/operation 604, a computing entity (such as the data object computing entity 105 described above in connection with FIG. 1 and FIG. 2) may include means (such as the processing element 205 of the data object computing entity 105 described above in connection with FIG. 2) to retrieve a client profile data object.

For example, the processing element may retrieve a client profile data object from a database (such as, but not limited to, the database 501 illustrated and described above in connection with FIG. 5). In some embodiments, the processing element may retrieve the client profile data object based at least in part on a client identifier. In the present disclosure, the term "client identifier" refers to an identifier that uniquely identifies data and information (such as, but not limited to, client profile data object) stored in a network computer system that is related to a client (such as a patient). In some embodiments, a client identifier may comprise ASCII text, a pointer, a memory address, and the like.

In some embodiments, the processing element may retrieve a plurality of client profile data objects at step/operation 604, and may determine whether to select each of the plurality of client profile data objects based at least in part on individual analysis for each of the plurality of client profile data objects in accordance with step/operation 606, step/operation 608, step/operation 610, and/or step/operation 612 of FIG. 6 described herein.

Referring back to FIG. 6, subsequent to step/operation 604, the example method 600 proceeds to step/operation 606. At step/operation 606, a computing entity (such as the data object computing entity 105 described above in connection with FIG. 1 and FIG. 2) may include means (such as the processing element 205 of the data object computing entity 105 described above in connection with FIG. 2) to retrieve a WGS data object related to the client profile data object retrieved at step/operation 604 and related to a disease identifier.

As described above, the WGS data object may represent, indicate, store and/or comprise data and/or information associated with the DNA sequence of a patient/client associated with the client profile data object retrieved at step/operation 604. In some embodiments, the WGS data object may comprise a PRS metadata and/or PRS-PheWAS metadata associated with the client profile data object and a disease identifier.

In some embodiments, the disease identifier may be programmatically or manually selected. For example, the processing element may retrieve data and/or information from one or more public databases (such as, but not limited to the Human Cell Atlas and/or GTEx), and may select a disease identifier corresponding to a disease that is associated with multiple causal genetic variants based at least in part on data and/or information from the one or more public databases. In some embodiments, the processing element may select a disease identifier corresponding to a disease where there is a temporal trajectory of consistent differential expression patterns in the disease-relevant tissue(s) based at least in part on data and/or information retrieved from the public databases. Examples of such diseases may include, but not limited to, T1D, NSCLC, and/or the like.

For example, the WGS data object may comprise a PRS metadata indicating a PRS for NSCLC (as indicated by the disease identifier) and associated with the client profile data object related to patient/client John.

Referring back to FIG. 6, subsequent to step/operation 606, the example method 600 proceeds to step/operation 608. At step/operation 608, a computing entity (such as the data object computing entity 105 described above in connection with FIG. 1 and FIG. 2) may include means (such as the processing element 205 of the data object computing entity 105 described above in connection with FIG. 2) to determine whether the WGS data object satisfies a threshold.

As described above, in some embodiments, the at least one WGS data object comprises at least one of at least one PRS metadata related to the disease identifier and/or at least one PRS-PheWAS metadata related to the disease identifier. In some embodiments, the processing element may retrieve at least one threshold related to the disease identifier and associated with the PRS metadata. In some embodiments, the processing element may retrieve at least one threshold related to the disease identifier and associated with the PRS-PheWAS metadata.

In some embodiments, the processing element may programmatically generate the at least one threshold associated with the WGS data object. For example, the processing element may retrieve data and/or information from public databases described above, and may programmatically generate the at least one threshold based at least in part on such data and/or information. In some embodiments, the processing element may receive one or more thresholds as inputs from one or more client computing entities.

In some embodiments, the at least one threshold associated with the WGS data object may categorize the WGS data object based at least in part on high risk, medium risk, and low risk. For example, the at least one threshold may comprise a threshold value indicating a maximum (and/or minimum) number of a PRS associated with a disease for a patient to be considered as having a low risk for that disease, a threshold value indicating a maximum (and/or minimum) number of a PRS associated with the disease for a patient to be considered as having a medium risk for that disease, and a threshold value indicating a maximum (and/or minimum) number of a PRS associated with the disease for a patient to be considered as having a high risk for that disease.

In some embodiments, the threshold may be in the form of a range. For example, the threshold may be in the form of a range of 1.10-1.17. If the PRS falls within the range, the processing element determines that the WGS data object corresponding to the PRS satisfies the threshold. If the PRS does not fall within the range, the processing element determines that the WGS data object corresponding to the PRS does not satisfy the threshold.

In some embodiments, the threshold may be in the form of a percentile based at least in part on a distribution of PRSs associated with a plurality of client profile data objects. For example, the threshold value of the threshold may be set as the top x % (for example, top 5%) of the PRSs. If PRS falls within the top 5% of the PRSs, the processing element may determine that the PRS satisfies the threshold. If the PRS does not fall within the top 5% of the PRSs, the processing element may determine that the PRS does not satisfy the threshold.

Referring back to FIG. 6, if, at step/operation 608, the processing element determines that the WGS data object satisfies the threshold, the example method 600 proceeds to step/operation 610. At step/operation 610, a computing entity (such as the data object computing entity 105 described above in connection with FIG. 1 and FIG. 2) may include means (such as the processing element 205 of the data object computing entity 105 described above in connection with FIG. 2) to select the client profile data object.

Continuing from the example above where the PRS is a number, if the PRS associated with the WGS data object is a positive value, the processing element may determine that the WGS data object satisfies the threshold if the PRS equals to or is higher than the threshold value associated with the threshold. If the PRS associated with the WGS data object is a negative value, the processing element may determine that the WGS data object satisfies the threshold if the PRS equals to or is less than the threshold value associated with the threshold.

In some embodiments, after the processing element selects the client profile data object, the processing element may utilize the client profile data object to generate a dynamic multigraph data object in accordance with various example methods described herein, including but not limited to, those described above in connection with at least FIG. 4 and FIG. 7.

Referring back to FIG. 6, if, at step/operation 608, the processing element determines that the WGS data object does not satisfy the threshold, the example method 600 proceeds to step/operation 612. At step/operation 612, a computing entity (such as the data object computing entity 105 described above in connection with FIG. 1 and FIG. 2) may include means (such as the processing element 205 of the data object computing entity 105 described above in connection with FIG. 2) to forgo selecting the client profile data object.

Continuing from the example above where the PRS is a number, if the PRS associated with the WGS data object is a positive value, the processing element may determine that the WGS data object does not satisfy the threshold if the PRS is lower than the threshold value associated with the threshold. If the PRS associated with the WGS data object is a negative value, the processing element may determine that the WGS data object does not satisfy the threshold if the PRS is higher than the threshold value associated with the threshold.

In some embodiments, after the processing element forgoes selecting the client profile data object, the client profile data object is not utilized in generating a dynamic multigraph data object.

Referring back to FIG. 6, subsequent to step/operation 610 and/or step/operation 612, the example method 600 proceeds to step/operation 614 and ends.

Referring now to FIG. 7, an example method 700 illustrates an example of generating at least one dynamic multigraph data object in accordance with embodiments of the present disclosure. In particular, the example method 700 illustrates an example of generating at least one dynamic multigraph data object based at least in part on calculating at least one differential expression metadata.

As shown in FIG. 7, the example method 700 starts at step/operation 701. Subsequent to step/operation 701, the example method 700 proceeds to step/operation 703. At step/operation 703, a computing entity (such as the data object computing entity 105 described above in connection with FIG. 1 and FIG. 2) may include means (such as the processing element 205 of the data object computing entity 105 described above in connection with FIG. 2) to retrieve at least one initial transcriptome data object and at least one subsequent transcriptome data object.

In some embodiments, the processing element may retrieve the at least one initial transcriptome data object and at least one subsequent transcriptome data object similar to those described above in connection with at least step/operation 406 of FIG. 4. For example, the at least one initial transcriptome data object comprises at least one initial tissue-relevant transcriptome metadata associated with the disease identifier. In some embodiments, the at least one subsequent transcriptome data object comprises at least one subsequent tissue-relevant transcriptome metadata associated with the disease identifier. Additionally, or alternatively, the at least one initial transcriptome data object comprises at least one initial scRNA-seq assay metadata associated with the disease identifier. In some embodiments, the at least one subsequent transcriptome data object comprises at least one subsequent scRNA-seq assay metadata associated with the disease identifier.

For example, the processing element may retrieve an initial scRNA-seq assay metadata related to NSCLC and associated with a client profile data object related to a patient/client John, and may retrieve one or more subsequent scRNA-seq assay metadata related to NSCLC and associated with John's client profile data object. In this example, the initial scRNA-seq assay metadata may be generated based at least in part on RNA of a cell or tissue of John that is related to the NSCLC and is collected and/or sampled in association with an initial date (for example, on the same date when John's DNA is collected and/or sampled for generating a WGS data object). The subsequent scRNA-seq assay metadata may be generated based at least in part on RNA of a cell or tissue of John that is related to the NSCLC and collected and/or sampled subsequent to the initial date (for example, in association with one or more clinical events represented by one or more clinical event data objects described herein).

Referring back to FIG. 7, subsequent to step/operation 703, the example method 700 proceeds to step/operation 705. At step/operation 705, a computing entity (such as the data object computing entity 105 described above in connection with FIG. 1 and FIG. 2) may include means (such as the processing element 205 of the data object computing entity 105 described above in connection with FIG. 2) to calculate at least one differential expression metadata.

In some embodiments, the processing element may calculate the at least one differential expression metadata based at least in part on the at least one initial transcriptome data object and the at least one subsequent transcriptome data object retrieved at step/operation 703. As described above, a differential expression metadata may represent, indicate, store and/or comprise data/information associated with difference(s) of gene expressions between two or more transcriptome data objects, between two or more tissue-relevant transcriptome metadata, and/or between two or more scRNA-seq assay metadata.

For example, the processing element may calculate the differential expression metadata based at least in part on comparing a subsequent transcriptome data object with an initial transcriptome data object to identify one or more differences, comparing a subsequent tissue-relevant transcriptome metadata with an initial tissue-relevant transcriptome metadata to identify one or more differences, and/or comparing a subsequent scRNA-seq assay metadata with an initial scRNA-seq assay metadata to identify one or more differences.

Additionally, or alternatively, the processing element may retrieve multiple subsequent transcriptome data objects at step/operation 703. In the examples, the processing element may calculate the differential expression metadata based at least in part on comparing a later subsequent transcriptome data object with an earlier subsequent transcriptome data object to identify one or more differences, comparing a later subsequent tissue-relevant transcriptome metadata with an earlier subsequent tissue-relevant transcriptome metadata to identify one or more differences, and/or comparing a later subsequent scRNA-seq assay metadata with an earlier subsequent scRNA-seq assay metadata to identify one or more differences.

Continuing from the example above, the processing element may calculate one or more differential expression metadata based at least in part on comparing the differences between the subsequent scRNA-seq assay metadata and the initial scRNA-seq assay metadata, and/or the differences between a later subsequent scRNA-seq assay metadata and an earlier subsequent scRNA-seq assay metadata, and/or the like.

Referring back to FIG. 7, subsequent to step/operation 705, the example method 700 proceeds to step/operation 707. At step/operation 707, a computing entity (such as the data object computing entity 105 described above in connection with FIG. 1 and FIG. 2) may include means (such as the processing element 205 of the data object computing entity 105 described above in connection with FIG. 2) to generate at least one dynamic multigraph data object.

In some embodiments, the processing element may generate the at least one dynamic multigraph data object based at least in part on the at least one differential expression metadata calculated at step/operation 705. As described above, the dynamic multigraph data object may be in the form of a data graph that comprises one or more dynamically generated nodes. As such, the processing element may encode the at least differential expression metadata calculated at step/operation 705 as one or more nodes in the data graph of the dynamic multigraph data object.

In some embodiments, such nodes may be associated with temporal information in the dynamic multigraph data object. For example, the processing element may calculate a differential expression metadata based at least in part on comparing a subsequent transcriptome data object with an initial transcriptome data object, generate a node based at least in part on the differential expression metadata, and associate the node with a temporal identifier of the subsequent transcriptome data object (and/or a temporal identifier indicating a time difference between the temporal identifiers of the subsequent transcriptome data object and the initial transcriptome data object).

While the description above provides an example of generating a dynamic multigraph data object, it is noted that the scope of the present disclosure is not limited to the description above. In some examples, an example dynamic multigraph data object may be generated based at least in part on one or more additional and/or alternative data and/or information.

For example, the processing element may generate the at least one dynamic multigraph data object based at least in part on one or more temporal identifiers. As described above, a temporal identifier may be in the form of a time code or a time stamp that identifies the date and/or time associated with a WGS data object and/or a transcriptome data object (for example, a tissue-relevant transcriptome metadata, a scRNA-seq assay metadata). In some embodiments, the processing element may generate a node on a time axis for each of the temporal identifiers, and may generate one or more edges connecting each of the nodes to a corresponding WGS data object or a corresponding transcriptome data object. Additional details are described herein, including, but not limited to, those described in connection with at least FIG. 8.

Referring back to FIG. 7, subsequent to step/operation 707, the example method 700 proceeds to step/operation 709 and ends.

While the description above provides an example of calculating differential expression metadata in the context of generating a dynamic multigraph data object, it is noted that the scope of the present disclosure is not limited to the description above. In some examples, an example differential expression metadata may be calculated by a TGN during the training of the TGN and/or for generating a risk window prediction data object, details of which are described in connection with at least FIG. 9 and FIG. 11.

Referring now to FIG. 8, an example diagram 800 is shown. In particular, the example diagram 800 illustrates an example dynamic multigraph data object in accordance with various embodiments of the present disclosure.

As described above, in some embodiments, the processing element may select a disease identifier corresponding to a specified disease for which there has been evidentiary support that the specified disease is associated with one or multiple causal genetic variants.

In some embodiments, example diseases associated with disease identifiers may include, but not limited to, T1D. In some embodiments, an example disease is related to one specific cell or tissue type, such as, but not limited to, lung tissue in the case NSCLC. In some embodiments, an example disease may be associated with more than one cell or tissue type, such as, but not limited to, cellular components of the adaptive immune system in the case of autoimmune disease.

For example, various data objects illustrated in FIG. 8, including but are not limited to, the initial transcriptome data object 802, the WGS data object 804, the subsequent transcriptome data object 806, the clinical event data object 808, the subsequent transcriptome data object 810, and the clinical event data object 812, may be associated with the disease identifier corresponding to NSCLC.

In some embodiments, a PRS can be constructed to conduct risk-scoring on a cohort of patients/clients of interest. For example, the PRS may be utilized to select one or more patients/clients for the cohort. Accordingly, an example processing element may select at least one client profile data object based at least in part on the PRS as described herein.

For example, various data objects illustrated in FIG. 8, including but are not limited to, the initial transcriptome data object 802, the WGS data object 804, the subsequent transcriptome data object 806, the clinical event data object 808, the subsequent transcriptome data object 810, and the clinical event data object 812, may be associated with a patient/client John who is associated with a PRS of NSCLC that satisfies a threshold.

As shown in FIG. 8, the WGS data object 804 is associated with a temporal identifier TO, which may indicate an index date on which the PRS or PRS-PheWAS is conducted. In some embodiments, on the index date of when the PRS is conducted (or, additionally, or alternatively, when a PRS-PheWAS is conducted), a baseline or initial scRNA-seq assay metadata of the tissue associated with the disease in question is also captured. In some embodiments, the baseline or initial scRNA-seq assay metadata may be part of a transcriptome data object associated with the client profile data object. As shown in FIG. 8, the initial transcriptome data object 802 is also associated with the temporal identifier TO.

Continuing from the example above, both the PRS metadata and the initial scRNA-seq assay metadata may be captured on the index date associated with the temporal identifier TO. For example, the RNA of a lung tissue of John may be captured or sampled on the index date associated with the temporal identifier TO, and the initial scRNA-seq assay metadata may be generated based at least in part on the RNA. In this example, the initial transcriptome data object 802 comprises the initial scRNA-seq assay metadata, and thus is associated with the temporal identifier TO.

As described above, each patient in the cohort is tracked from the date when their initial PRS is calculated. In some embodiments, when there is a significant clinical event related to a patient in the cohort that is deemed to be potentially associated with the disease that has been risk-scored, a subsequent scRNA-seq assay metadata is captured.

In the example shown in FIG. 8, the clinical event data object 808 and the subsequent transcriptome data object 806 are associated with the temporal identifier T1, and the subsequent transcriptome data object 810 and the clinical event data object 812 are associated with the temporal identifier T2.

In some embodiments, the clinical event data object 808 may be associated with a significant clinical event on the index date associated with the temporal identifier T1 that is related to the patient/client and associated with the disease of interest, and a subsequent scRNA-seq assay metadata is generated to capture a subsequent scRNA-seq assay conducted on the index date associated with the temporal identifier T1. In some embodiments, the subsequent transcriptome data object 806 may comprise the subsequent scRNA-seq assay metadata, and is thus also associated with the temporal identifier T1.

In some embodiments, the clinical event data object 812 may be associated with a significant clinical event on the index date associated with the temporal identifier T2 that is related to the patient/client and associated with the disease of interest, and a subsequent scRNA-seq assay metadata is generated to capture a subsequent scRNA-seq assay conducted on the index date associated with the temporal identifier T2. In some embodiments, the subsequent transcriptome data object 810 may comprise the subsequent scRNA-seq assay metadata, and is thus also associated with the temporal identifier T2.

Continuing from the example above, if the patient/client John has a high PRS for NSCLC and then is diagnosed with pneumonia at a clinical event (for example, during a doctor's visit or in-patient treatment), a corresponding subsequent clinical event data object (for example, the clinical event data object 808) is generated. Even without any evidence of the onset of any NSCLC, it is possible that this clinical event may impact the risk trajectory for NSCLC, and thus a corresponding scRNA-seq assay would be performed (for example, may also be stored as part of the subsequent transcriptome data object 806).

In some embodiments, any patient in the cohort that has clinically-determined fully symptomatic onset of the disease in question has the index date of onset noted as a data point, which may represent the endpoint of the trial. As shown in FIG. 8, the processing element may retrieve a validated onset temporal metadata 814 that indicates an index date T3 of disease onset that has been clinically validated.

In some embodiments, a processing element may generate a dynamic multigraph data object based at least in part on the clinical event data objects and transcriptome data objects.

For example, for a client profile data object selected from at least one client profile data object, a corresponding initial transcriptome data object of the at least one initial transcriptome data object and a corresponding WGS data object of the at least one WGS data object are associated with an initial temporal identifier. In the example shown in FIG. 8, the processing element may identify the initial temporal identifier T0 indicating a baseline index date associated with the WGS data object 804 and the initial transcriptome data object 802, and may generate a node corresponding to the baseline temporal identifier T0. The processing element may generate a node corresponding to the WGS data object 804 and a node corresponding to the initial transcriptome data object 802. The processing element may generate an edge connecting the node corresponding to the temporal identifier T0 to the node corresponding to the WGS data object 804, and may generate an edge connecting the node corresponding to the temporal identifier T0 to the node corresponding to the initial transcriptome data object 802.

Additionally, or alternatively, for the client profile data object selected from at least one client profile data object, a corresponding subsequent transcriptome data object of the at least one subsequent transcriptome data object and a corresponding clinical event data object of the at least one clinical event data object are associated with a corresponding subsequent temporal identifier. In the example shown in FIG. 8, the processing element may identify a subsequent temporal identifier T1 indicating an index date associated with the clinical event data object 808 and the subsequent transcriptome data object 806, and may generate a node corresponding to the subsequent temporal identifier T1. The processing element may generate a node corresponding to the clinical event data object 808 and a node corresponding to the subsequent transcriptome data object 806. The processing element may generate an edge connecting the node corresponding to the temporal identifier T1 to the node corresponding to the clinical event data object 808, and may generate an edge connecting the node corresponding to the temporal identifier T1 to the node corresponding to the subsequent transcriptome data object 806.

In some embodiments, the processing element may generate at least one dynamic multigraph data object based at least in part on the initial temporal identifier and the one or more subsequent temporal identifiers. In the example shown in FIG. 8, the node corresponding to the baseline temporal identifier T0 and the temporal identifier T1 are positioned on a time axis based at least in part on their corresponding dates. In some embodiments, the position of a subsequent temporal identifier (for example, T1) on the time axis correlates to the elapsed time from index date of the initial temporal identifier (for example, T0).

Similarly, the processing element may generate one or more additional nodes based at least in part on additional clinical event data objects and additional subsequent transcriptome data objects. As such, the dynamic multigraph data object can be dynamically updated as more clinical event data objects and transcriptome data objects are generated.

In the example shown in FIG. 8, different clinical event data objects may be positioned differently with respect to the temporal identifier based at least in part on the corresponding clinical event type. For example, the clinical event data object 808 is positioned upwards with respect to the temporal identifier T1, which may indicate that the clinical event data object 808 is associated with one type of clinical event (for example, an impatient episode). As another example, the clinical event data object 812 is positioned downwards with respect to the temporal identifier T2, which may indicate that the clinical event data object 812 is associated with a different type of clinical event (for example, an acute illness with no impatient stay).

In some embodiments, a processing element may calculate a differential expression metadata that indicates a disease-relevant differential gene expression of the subsequent scRNA-seq assay metadata as compared to the baseline or initial scRNA-seq assay metadata. In some embodiments, the differential expression metadata is utilized by a TGN to generate a risk window prediction data object, details of which are described herein. In some embodiments, the TGN may generate the differential expression metadata for training and/or for generating a risk window prediction data object, details of which are described herein.

As shown in FIG. 8, the processing element may calculate differential expression metadata based at least in part on comparing differences between the scRNA-seq assay metadata 53 LEGAL02/40684941v7 associated with the subsequent transcriptome data object 806 and the scRNA-seq assay metadata associated with the initial transcriptome data object 802. Additionally, or alternatively, the processing element may calculate differential expression metadata based at least in part on comparing difference between the scRNA-seq assay metadata associated with the subsequent transcriptome data object 810 and the scRNA-seq assay metadata associated with the initial transcriptome data object 802. Additionally, or alternatively, the processing element may calculate differential expression metadata based at least in part on comparing difference between the scRNA-seq assay metadata associated with the subsequent transcriptome data object 810 and the scRNA-seq assay metadata associated with the subsequent transcriptome data object 806.

Continuing from the example above, the processing element may calculate a differential expression metadata based at least in part on the differential expression of the subsequent scRNA-seq assay metadata associated with John's lung tissue as compared to the initial scRNA-seq assay metadata associated with John's lung tissue.

As such, in the example shown in FIG. 8, the initial temporal identifier TO may be associated with an index date for which a PRS metadata (for example, as shown in the WGS data object 804) is generated for a disease (for example, T1D). As the PRS associated with the PRS metadata is high, an initial transcriptome data object 802 is also generated and may correspond to a baseline whole transcriptome assay (for example, for pancreatic tissue).

In some embodiments, the clinical event data object 808 may be associated with an interaction with care provider that indicates evidence of dysglycaemia (which is associated with T1D), and a corresponding subsequent transcriptome data object 806 is generated that may comprise RNA-seq or scRNA-seq on pancreatic tissue that has been sampled on the date associated with the clinical event data object 808 (e.g. the index date corresponding to the temporal identifier T1) in order to compute differential expression metadata as compared to that of the initial transcriptome data object 802. Additionally, or alternatively, co-incident or temporally close EMRs and/or claim data may also be analyzed.

In some embodiments, the clinical event data object 812 may be associated with manifestations of clinical symptoms of T1D, such as, but not limited to, polyuria, diabetic ketoacidosis, polydipsia, and/or the like (which is associated with T1D), and a corresponding subsequent transcriptome data object 810 is generated that may comprise RNA-seq or scRNA-seq on pancreatic tissue that has been sampled on the date associated with the clinical event data object 812 in order to compute differential expression metadata as compared to that of the initial transcriptome data object 802. Additionally, or alternatively, co-incident or temporally close EMRs and/or claim data may also be analyzed.

While FIG. 8 provides an example illustration of an example dynamic multigraph data object, it is noted that the scope of the present disclosure is not limited to the description above. In some examples, an example dynamic multigraph data object may comprise one or more additional and/or alternative elements (such as, but not limited to, differential expression metadata described above).

As such, in accordance with various embodiments of the present disclosure, at least one dynamic multigraph data object may be generated based at least in part on data and/or information associated with a selected cohort of patients.

In some embodiments, an example method may calculate a PRS metadata using the most accurate technique, including, but not limited to, open-source software tools such as LDpred. The PRS calculation is used as a baseline: if the risk of a disease (for example, T1D) is predicted to be significant, this makes the trilateration of estimated time window more effective, as the underlying signal strength for T1D in this particular patient is more likely to occur.

In some embodiments, an example method may include determining whether a single tissue type or multiple tissue types are involved in a specific disease. In some embodiments, a PRS-PheWAS may be a more effective method for baselining the risk than a PRS if multiple tissue types are involved (for example, cancers).

In some embodiments, after determining a disease to consider, the example method may determine that there is a temporal trajectory of consistent differential expression patterns in the disease-relevant tissue(s). For example, an example method may retrieve data and/or information (for example, from a partnership with a university department of molecular biology that includes performing experimental studies on models). Based at least in part on the data and/or information, the example method may determine whether there is sufficient evidence to proceed. For example, if, in murine models such as NOD mice, there is a temporal trajectory of differential expression patterns linked to disease pathogenesis, then the example method may comprise formulating a clinical trial associated with a cohort of patients. In some embodiments, to refine the approach, example methods of the present disclosure may obtain data and/or information assisted with details for tissue RNA expression, which may be available in public databases such as the Human Cell Atlas and GTEx, to validate scRNA-seq tissue expression data.

In some embodiments, the example method may include selecting a cohort of patients for which risk-scoring for a given disease is desirable, and select a disease to be risk-scored (e.g. T1D). In some embodiments, the example method may including obtain data and/or information from consultation with experts (such as, but not limited to, clinicians, pathologists, geneticists, epidemiologists, etc.), and determine whether a patient will undergo a PRS for the disease in question or a PRS-PheWAS is more applicable.

In some embodiments, the example method may select a sufficient number of patients as participants for analysis purposes, as well as appropriate consent has been established for participants. In some embodiments, client profile data objects associated with the patients (for example, EMR data) should meet completeness requirements for key data features (e.g. EMR fields).

In some embodiments, the client profile data objects associated with the patients (such as the patient's longitudinal EMRs) are manually reviewed or via an automated alert system to identify significant clinical events, such as in-patient hospitalizations or major diagnostic tests (e.g. CT imaging study). In some embodiments, an alert system will be implemented as per standard EMR alerting capabilities, depending upon the EMR software vendor. Each event that may be of relevance to the disease under consideration may alert the patient's care provider, and the software vender or the patient's care provider may determine whether an initiation of scRNA-seq is appropriate.

In some embodiments, for each patient in the cohort, the example method may perform PRS and then perform baseline scRNA-seq on the determined tissue, e.g. perform scRNA-seq on pancreatic tissue for T1D. In some embodiments, the clinical trial may be in a form similar to a cross-sectional study.

In some embodiments, for the disease of interest, the example method may determine characteristic clinical events that may be associated with increased likelihood of risk from the relevant research literature and/or input from clinical experts (e.g. an episode of dysglycaemia for a pre-diabetic patient indicates a 75% risk of T1D occurrence).

At the occurrence of each determined event, the example method may perform a scRNA-seq analysis for that patient and associate the scRNA-seq assay metadata from the scRNA-seq analysis with the index date of that clinical event (e.g. an episode of dysglycaemia on Jan. 1, 2021 would result in a pancreatic scRNA-seq assay to be performed on that day and the results stored). In some embodiments, for patients associated with a determined event, an estimate of the likelihood of occurrence is stored in the client profile data object (e.g. the 75% increased risk after dysglycaemia) as additional clinical data.

In some embodiments, the example method may include providing these clinical event data, together with the event-associated scRNA-seq assay metadata and the scRNA-seq assay metadata from the time of initial PRS, to a graph database.

As described further herein, the example method may further include recording index dates of the confirmed symptomatic onset of the disease under consideration for each patient. In some embodiments, such index dates are the target variable for the TGN. In some embodiments, the target variable has a relatively large region of uncertainty and, depending upon the exact formulation of the TGN, the example method may generate a confidence interval for the date of onset and/or the estimated probability of the window boundaries (e.g. analogously to a SoftMax layer in a multi-class classification deep neural network).

c. Exemplary Training of Temporal Graph Network (TGN)

As described above, analyzing dynamic multigraph data object requires specialized analysis methods, as it is the dynamic structure that contains critical insights about the system and how it evolves. TGN can be trained for a variety of tasks such as edge prediction (e.g. self-supervised) or node classification (e.g. semi-supervised). Various embodiments of the present disclosure may provide link prediction operations: provided a list of time ordered interactions, the link prediction operations predict future interactions from those observed in the past. Various embodiments of the present disclosure apply the TGN to a dynamic multigraph data object based at least in part on the cohort data in order to train on the TGN based at least in part on the dynamic multigraph data object that is associated with longitudinal clinical events and corresponding scRNA-seq data for the entire cohort under consideration, and the TGN may predict upper and lower bounds for the time of the "risk window" associated with the disease under consideration.

Figure 9:
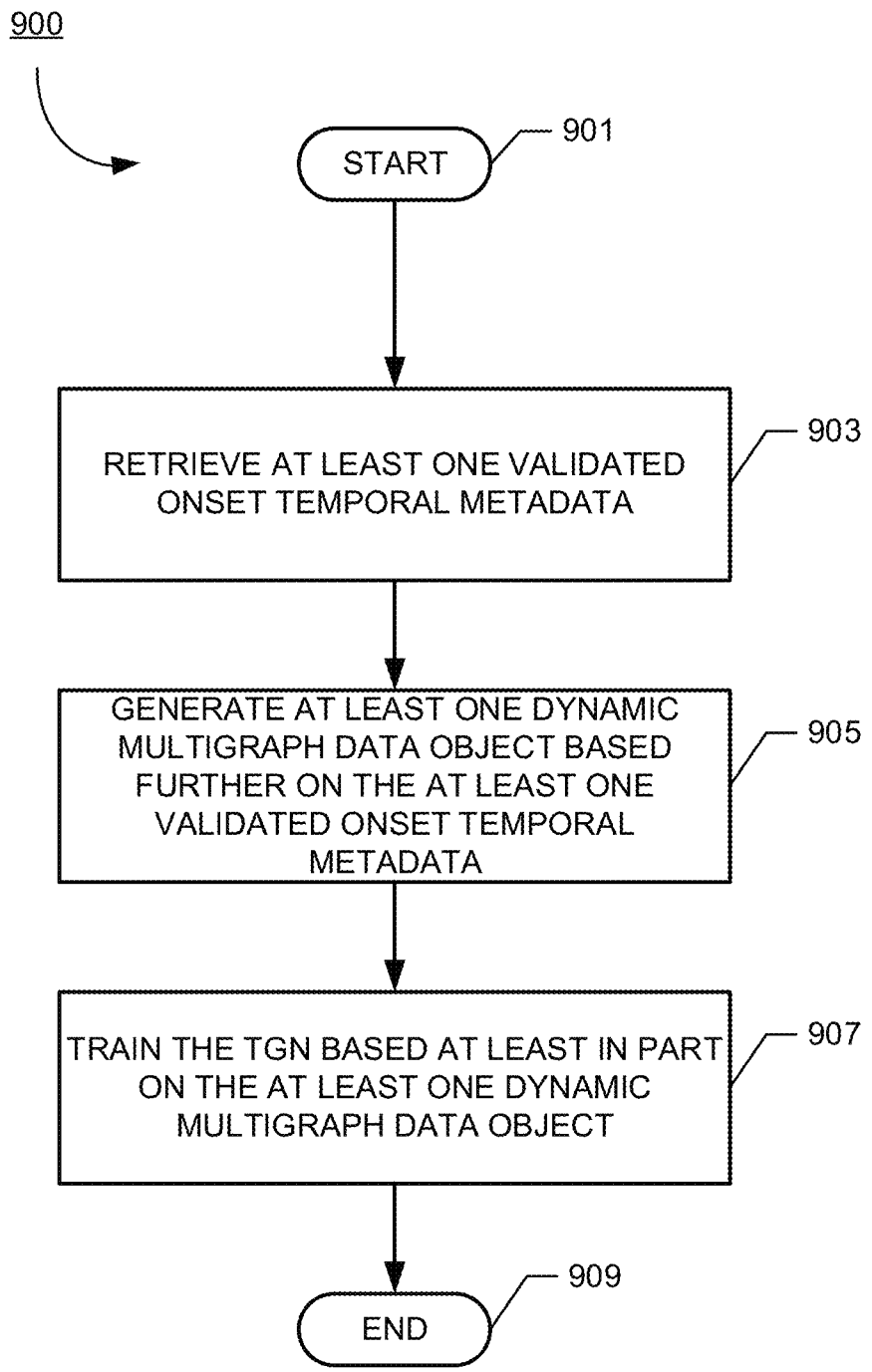
Figure 10:
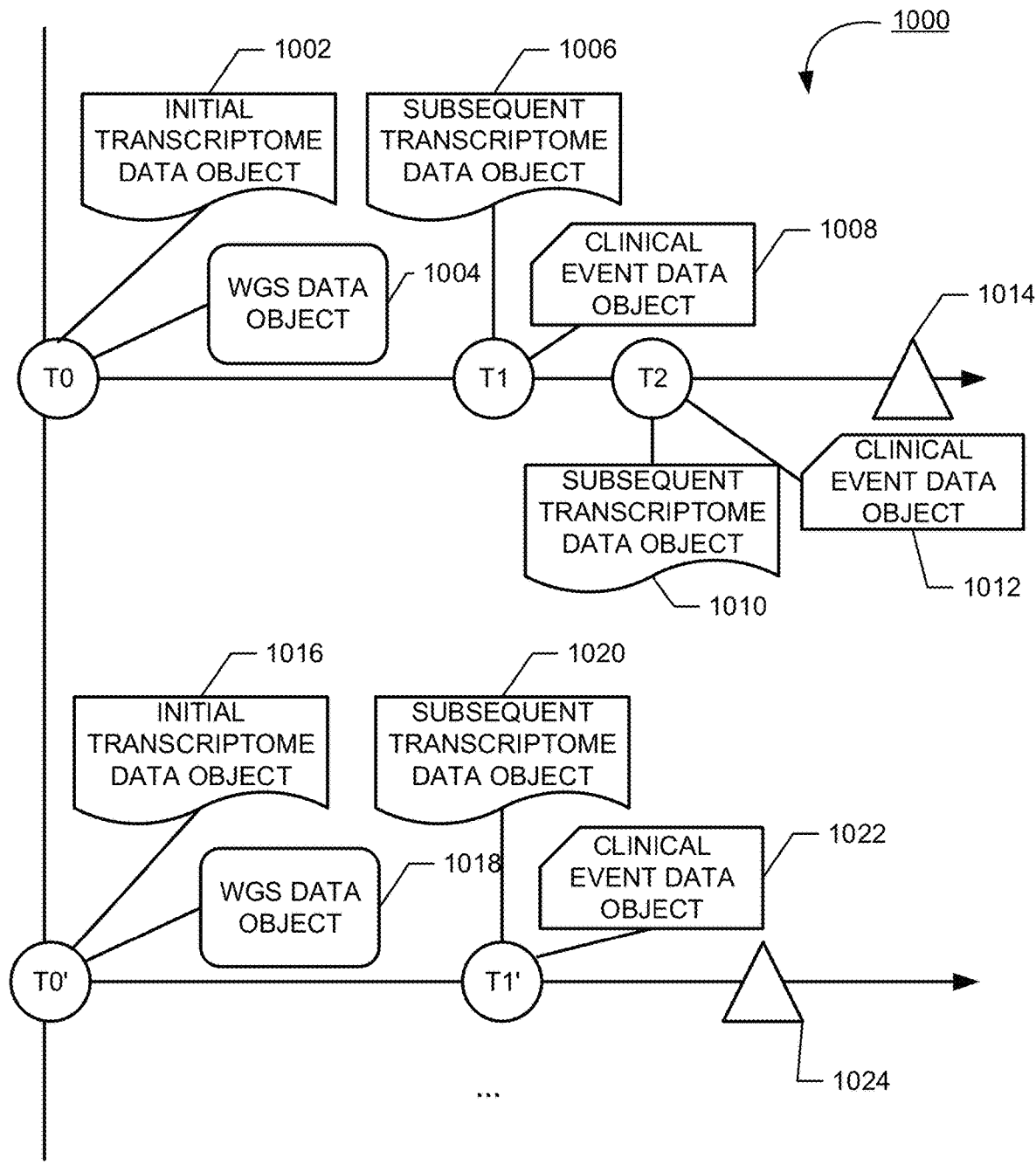

In various embodiments of the present disclosure, a computing entity (such as the data object computing entity 105 described above in connection with FIG. 1 and FIG. 2) may implement various processing techniques (including, but not limited to, one or more encoding and/or embedding techniques) to train a TGN (for example, in connection with at least step/operation 410 of FIG. 4 described above). Referring now to FIG. 9-FIG. 10, various examples associated with training a TGN are illustrated.

Referring now to FIG. 9, an example method 900 illustrates an example of training a TGN in accordance with embodiments of the present disclosure. In particular, the example method 900 illustrates an example of training a TGN based at least in part on at least one dynamic multigraph data object.

As shown in FIG. 9, the example method 900 starts at step/operation 901. Subsequent to step/operation 901, the example method 900 proceeds to step/operation 903. At step/operation 903, a computing entity (such as the data object computing entity 105 described above in connection with FIG. 1 and FIG. 2) may include means (such as the processing element 205 of the data object computing entity 105 described above in connection with FIG. 2) to retrieve at least one validated onset temporal metadata.

In some embodiments, the processing element may retrieve at least one validated onset temporal metadata associated with at least one client profile data object and a disease identifier.

In some embodiments, the at least one client profile data object may be selected in association with generating a dynamic multigraph data object, similar to those described in connection with at least FIG. 4 and FIG. 6. As such, the at least one validated onset temporal metadata is associated with at least one client profile data object that has been selected for generating a dynamic multigraph data object.

As described above, the validated onset temporal metadata refers to a type of metadata that may represent, indicate, store and/or comprise a time code or a time stamp that indicates a clinically validated date and/or time that a disease is onset in a patient/client. As such, the validated onset temporal metadata may be associated with a disease identifier and indicate a clinically validated date and/or time that a disease associated with the disease identifier is onset.

For example, the processing element may retrieve a validated onset temporal metadata associated with a client profile data object related to a patient/client John and a disease identifier associated with NSCLC. The validated onset temporal metadata may indicate a clinically validated date and/or time that NSCLC becomes onset in John.

Referring back to FIG. 9, subsequent to step/operation 903, the example method 900 proceeds to step/operation 905. At step/operation 905, a computing entity (such as the data object computing entity 105 described above in connection with FIG. 1 and FIG. 2) may include means (such as the processing element 205 of the data object computing entity 105 described above in connection with FIG. 2) to generate at least one dynamic multigraph data object based further on the at least one validated onset temporal metadata.

As described above, a processing element may generate at least one dynamic multigraph data object based at least in part on at least one initial transcriptome data object, at least one subsequent transcriptome data object, and at least one clinical event data object associated with at least one client profile data object. For example, to generate a dynamic multigraph data object, the processing element may generate a node on a time axis for each temporal identifier associated with the at least one initial transcriptome data object, the at least one subsequent transcriptome data object, and/or the at least one clinical event data object, and may generate one or more edges connecting each of the nodes to a node corresponding to an initial transcriptome data object, a subsequent transcriptome data object, and/or a clinical event data object.

In some embodiments, the processing element may further generate a node on the time axis corresponding to the at least one validated onset temporal metadata. For example, the processing element may position the at least one validated onset temporal metadata based at least in part on the date and/or time that the disease becomes fully symptomatic.

Continuing from the example above, the processing element may generate a dynamic multigraph data object based at least in part on the at least one initial transcriptome data object, the at least one subsequent transcriptome data object, and the at least one clinical event data object associated with John. For example, the processing element may generate a node on a time axis for each temporal identifier associated with the at least one initial transcriptome data object, the at least one subsequent transcriptome data object, and the at least one clinical event data object associated with John, and may generate one or more edges connecting each of the nodes to a corresponding initial transcriptome data object, a corresponding subsequent transcriptome data object, and/or a corresponding clinical event data object associated with John. The processing element may further generate a node on the time axis corresponding to the date and/or time that the NSCLC becomes fully symptomatic in John based at least in part on the validated onset temporal metadata.

Referring back to FIG. 9, subsequent to step/operation 905, the example method 900 proceeds to step/operation 907. At step/operation 907, a computing entity (such as the data object computing entity 105 described above in connection with FIG. 1 and FIG. 2) may include means (such as the processing element 205 of the data object computing entity 105 described above in connection with FIG. 2) to train the TGN based at least in part on the at least one dynamic multigraph data object.

As described above, the at least one dynamic multigraph data object generated at step/operation 905 may comprise at least one validated onset temporal metadata. As such, the processing element may train the TGN based at least in part on the at least one validated onset temporal metadata.

For example, based at least in part on the dynamic multigraph data object, the processing element may cause the TGN to generate a risk window prediction data object that indicates an estimated or predicted time frame that the disease becomes fully symptomatic, and compare the risk window prediction data object with the validated onset temporal metadata. If the date and/or time indicated by the validated onset temporal metadata does not fall within the predicted time frame of the risk window prediction data object, the processing element may cause the TGN to adjust one or more of its parameters (for example, adjusting one or more parameters associated with the memory module, the message function module, the message updater module, message aggregator module, and/or the embedding module) until a predicted time frame of a risk window prediction data object generated by the TGN captures the date and/or time indicated by the validated onset temporal metadata.

In some embodiments, during training, the TGN may calculate at least one differential expression metadata (for example, based at least in part on at least those described above in connection FIG. 7 and FIG. 8 above). In such embodiments, the dynamic multigraph data objects provided to the TGN may not comprise the at least one differential expression metadata. The TGN may generate at least one risk window prediction data object based at least in part on the at least one differential expression metadata. For example, the TGN may compare genetic sequencing data (e.g. scRNA-seq assay metadata) at different points in time, thereby computing a temporal evolution of genetic expression in disease tissue that leads to the estimation of a time window of when the disease becomes onset.

Referring back to FIG. 9, subsequent to step/operation 907, the example method 900 proceeds to step/operation 909 and ends.

Referring now to FIG. 10, an example diagram 1000 is shown. In particular, the example diagram 1000 illustrates an example dynamic multigraph data object in accordance with various embodiments of the present disclosure.

In some embodiments, the processing element may generate a dynamic multigraph data object based at least in part on data and/or information associated with a disease identifier and a plurality of client profile data objects.

In the example shown in FIG. 10, the initial transcriptome data object 1002, the WGS data object 1004, the subsequent transcriptome data object 1006, the clinical event data object 1008, the subsequent transcriptome data object 1010, the clinical event data object 1012, the validated onset temporal metadata 1014, the initial transcriptome data object 1016, the WGS data object 1018, the subsequent transcriptome data object 1020, the clinical event data object 1022, and the validated onset temporal metadata 1024 are associated with the same disease identifier.

In the example shown in FIG. 10, the example dynamic multigraph data object may comprise one or more time axes, and each of the one or more time exes is associated with a signal patient's temporal progression of a disease.

For example, the initial transcriptome data object 1002, the WGS data object 1004, the subsequent transcriptome data object 1006, the clinical event data object 1008, the subsequent transcriptome data object 1010, the clinical event data object 1012, and the validated onset temporal metadata 1014 are associated with a first client profile data object. The processing element may generate nodes representing the initial temporal identifier T0, the subsequent temporal identifier T1, the subsequent temporal identifier T2, and the validated onset temporal metadata 1014, and position them on a time axis, similar to those described above. The processing element may generate an edge connecting a node representing the initial transcriptome data object 1002 to the node representing the initial temporal identifier T0, generate an edge connecting a node representing the WGS data object 1004 to the node representing the initial temporal identifier T0, generate an edge connecting a node representing the subsequent transcriptome data object 1006 to the node representing the subsequent temporal identifier T1, generate an edge connecting a node representing the clinical event data object 1008 to the node representing the subsequent temporal identifier T1, generate an edge connecting a node representing the subsequent transcriptome data object 1010 to the node representing the subsequent temporal identifier T2, and generate an edge connecting a node representing the clinical event data object 1012 to the node representing the subsequent temporal identifier T2, similar to those described above.

Additionally, or alternatively, the initial transcriptome data object 1016, the WGS data object 1018, the subsequent transcriptome data object 1020, the clinical event data object 1022, and the validated onset temporal metadata 1024 are associated with a second client profile data object. The processing element may generate nodes representing the initial temporal identifier T0', the subsequent temporal identifier T1', and the validated onset temporal metadata 1024, and position them on a time axis, similar to those described above. The processing element may generate an edge connecting a node representing the initial transcriptome data object 1016 to the node representing the initial temporal identifier T0', generate an edge connecting a node representing the WGS data object 1018 to the node representing the initial temporal identifier T0', generate an edge connecting a node representing the subsequent transcriptome data object 1020 to the node representing the subsequent temporal identifier T1', generate an edge connecting a node representing the clinical event data object 1022 to the node representing the subsequent temporal identifier T1', similar to those described above.

In some embodiments, the processing element may normalize the temporal identifiers related to data objects associated with different client profile data objects. In the example shown in FIG. 10, the processing element may generate an edge connecting the node corresponding to the initial temporal identifier TO and the node corresponding to the initial temporal identifier T0', and may position their corresponding time axes such that the starting positions of these axes (e.g. the node corresponding to the initial temporal identifier TO and the node corresponding to the initial temporal identifier T0') are along the same edge.

As described above, the dynamic multigraph data object may be dynamically updated. For example, as transcriptome data object(s), WGS data object(s), and/or clinical event data object(s) associated with one or more client profile data objects are generated, the processing element may generate node(s) corresponding to such data object(s) and generate edge(s) connecting such node(s), similar to those described above.

In some embodiments, an example method may generate a time series of differential expression metadata, which may then be compared with those associated with similar groups of clients/patients for training the TGN and/or generating a risk window prediction data object.

For example, the processing element may generate a first differential expression metadata based at least in part on the scRNA-seq assay metadata associated with the subsequent transcriptome data object 1006 and the scRNA-seq assay metadata associated with the initial transcriptome data object 1002. The processing element may generate a second differential expression metadata based at least in part on the scRNA-seq assay metadata associated with the subsequent transcriptome data object 1020 and the scRNA-seq assay metadata associated with the initial transcriptome data object 1016. The processing element may compare the first differential expression metadata with the second differential expression metadata in training the TGN and/or generating a risk window prediction data object.

In some embodiments, these time axes are converted to time series via clustering of events. For example, if multiple patients experience pneumonia as indicated by the corresponding clinical event data objects (for example, clinical event data object 1008 and clinical event data object 1022) prior to their eventual progression to fully symptomatic disease (for example, based at least in part on the validated onset temporal metadata 1014 and the validated onset temporal metadata 1024), it may indicate that the relevant differential expression analysis, such as the scRNA-seq assay metadata associated with these episodes of pneumonia compared to their baseline scRNA-seq assay metadata (for example, the subsequent transcriptome data object 1006 compared to the initial transcriptome data object 1002, and the subsequent transcriptome data object 1020 compared to the initial transcriptome data object 1016), can be an important predictor of the temporal onset of the risk-scored disease, and the associated differential expression metadata may be provided to train a TGN and/or generate a risk window prediction data object.

As such, in accordance with various embodiments of the present disclosure, a TGN may be trained based at least in part on dynamic multigraph data object(s) generated based at least in part on data and/or information such as, but not limited to, those related to clinical events, scRNA-seq data for relevant tissues to form differential expression patterns, index date for disease onset, and/or other relevant clinical data (e.g. HbA1c values in the case of T1D). In some embodiments, the TGN may be trained using the entire cohort as training data.

In some embodiments, a dynamic multigraph data object may contain time-dependent information that can be altered dynamically. For example, as time-dependent clinical event information occurs (together with associated scRNA-seq data), the processing element may generate a time series of differential gene expression patterns related to the disease under consideration, and an example TGN provides an ideal analysis tool for such dynamic multigraph data object.

In some embodiments, the TGN may be deployed on the cohort of patient data in the accordance with various example methods of deep learning (such as, but not limited to, cross-validation, feature engineering, pre-processing and re-casting) and based at least in part on differential expression data in a form amenable for training the TGN. For example, the TGN may be incorporated into a continuous learning paradigm, whereby "real-world" risk window prediction data objects generated by examples of the present disclosure are fed back into the TGN in order to refine and improve its accuracy (similar to the back-prop step in deep learning techniques). In some embodiments, the TGN may be implemented to test additional dynamic multigraph data objects and/or generate risk window prediction data objects based at least in part on these additional dynamic multigraph data objects. Additional details are described herein.

d. Exemplary Implementation of Temporal Graph Network (TGN)

Figure 11:
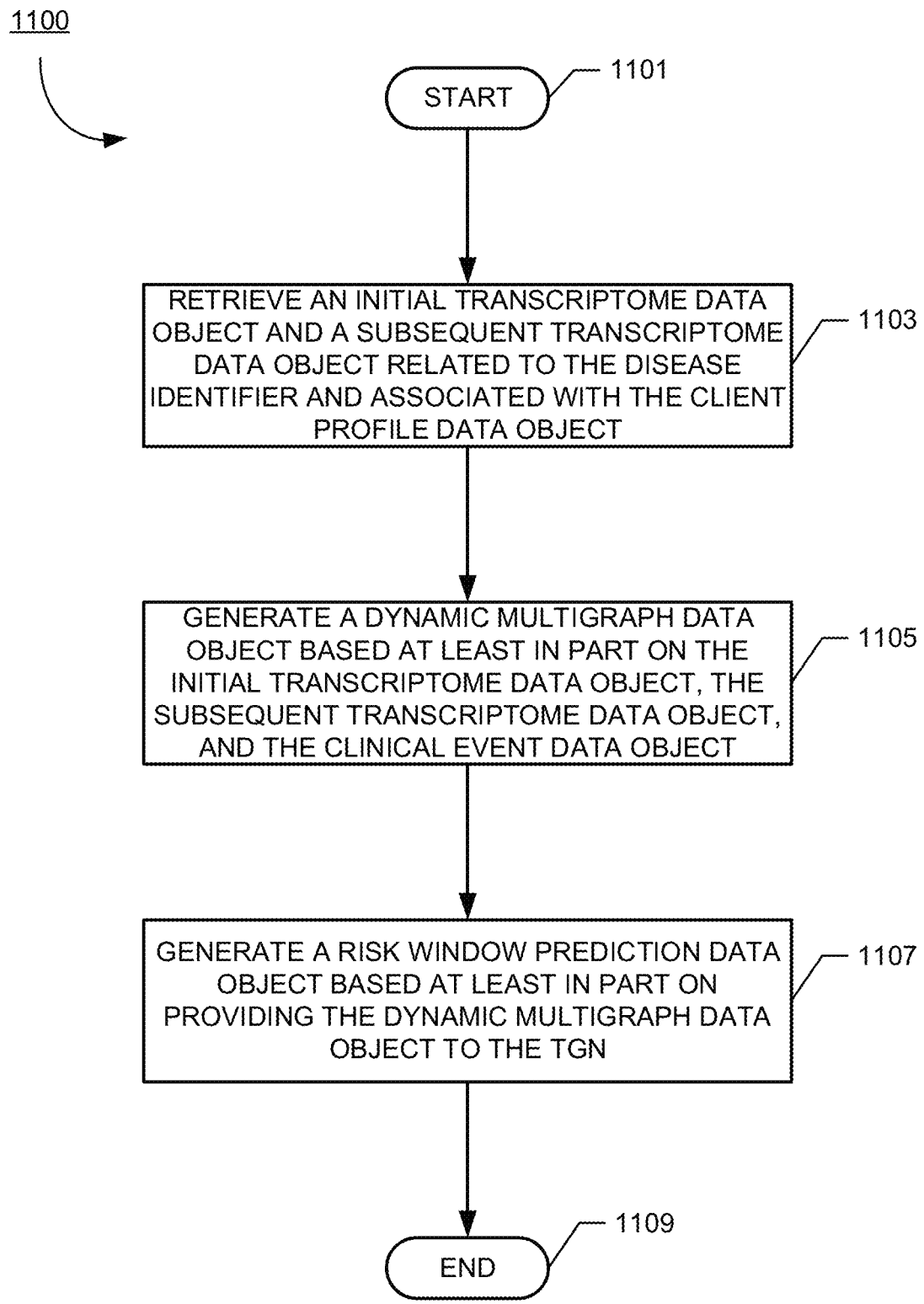
Figure 12:
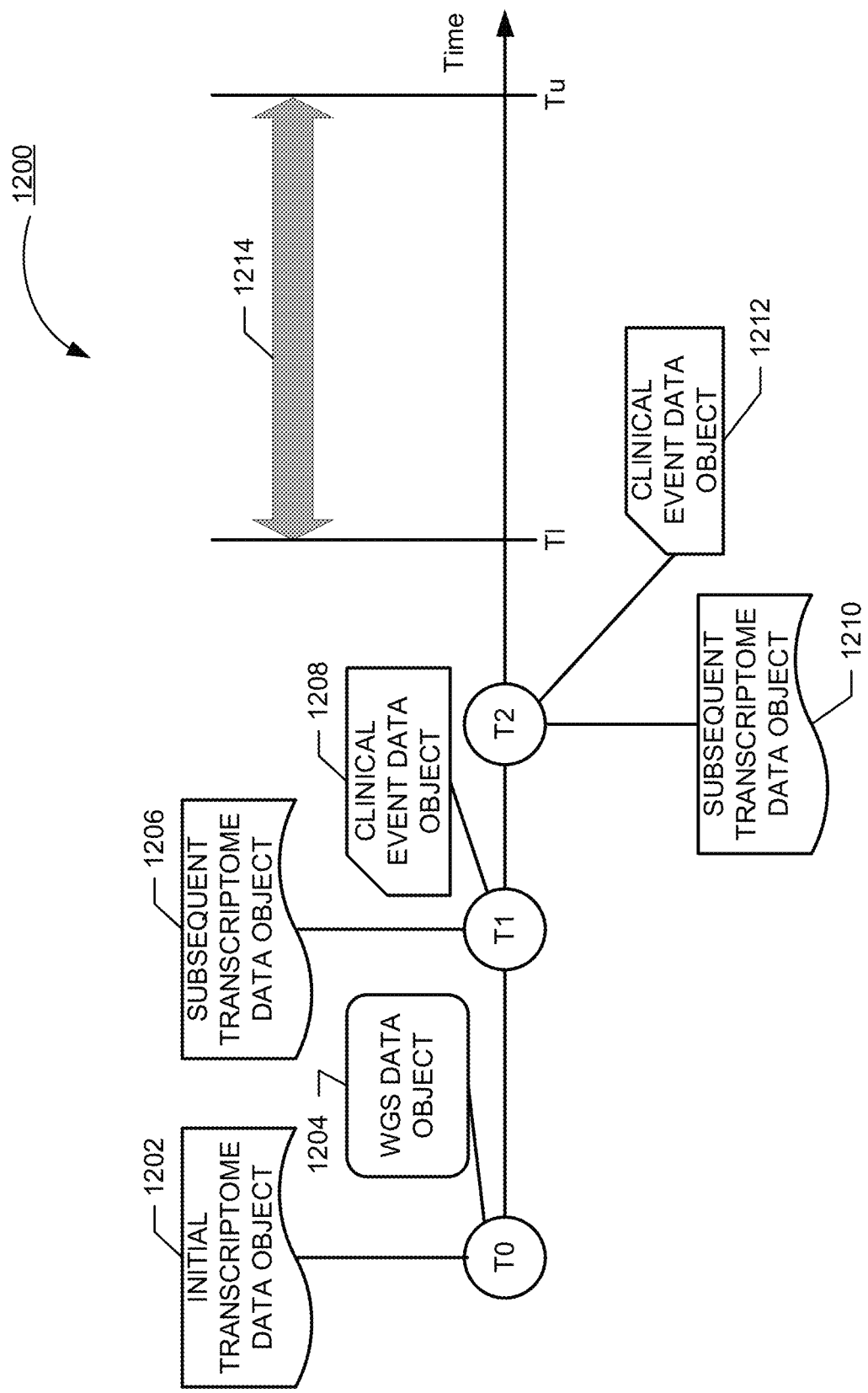

In various embodiments of the present disclosure, a computing entity (such as the data object computing entity 105 described above in connection with FIG. 1 and FIG. 2) may implement various processing techniques (including, but not limited to, one or more encoding and/or embedding techniques) to implement the TGN to generate a risk window prediction data object. Referring now to FIG. 11-FIG. 12, various examples associated with generating a risk window prediction data object are illustrated.

Referring now to FIG. 11, an example method 1100 illustrates an example of generating a risk window prediction data object in accordance with embodiments of the present disclosure. In particular, the example method 1100 illustrates an example of implementing a TGN to generate a risk window prediction data object.

As shown in FIG. 11, the example method 1100 starts at step/operation 1101. Subsequent to step/operation 1101, the example method 1100 proceeds to step/operation 1103. At step/operation 1103, a computing entity (such as the data object computing entity 105 described above in connection with FIG. 1 and FIG. 2) may include means (such as the processing element 205 of the data object computing entity 105 described above in connection with FIG. 2) to retrieve an initial transcriptome data object and a subsequent transcriptome data object related to a disease identifier and associated with a client profile data object.

For example, the processing element may retrieve an initial transcriptome data object and a subsequent transcriptome data object related to the disease identifier and associated with a client profile data object similar to those described above in connection with at least step/operation 406 of FIG. 4. In some embodiments, the subsequent transcriptome data object is associated with a clinical event data object.

As an example, the processing element may retrieve an initial transcriptome data object and a subsequent transcriptome data object related to a disease identifier indicating NSCLC and associated with a client profile data object related to a patient/client John. The subsequent transcriptome data object may be associated with a visit to doctor's office by John related to his chest pain. In this example, the subsequent transcriptome data object is associated with a clinical event data object that is related to the visit and comprises symptom metadata indicating chest pain.

Referring back to FIG. 11, subsequent to step/operation 1103, the example method 1100 proceeds to step/operation 1105. At step/operation 1105, a computing entity (such as the data object computing entity 105 described above in connection with FIG. 1 and FIG. 2) may include means (such as the processing element 205 of the data object computing entity 105 described above in connection with FIG. 2) to generate a dynamic multigraph data object based at least in part on the initial transcriptome data object, the subsequent transcriptome data object, and the clinical event data object.

In some embodiments, the processing element may generate the dynamic multigraph data object based at least in part on various example methods described herein, including, but not limited to, in connection with at least FIG. 4 to FIG. 8.

Continuing from the example above, the processing element may generate a dynamic multigraph data object that comprises a plurality of nodes connected on a time axis, each corresponding to a temporal identifier associated with one of the at least one initial transcriptome data object, the at least one subsequent transcriptome data object, and/or the at least one clinical event data object. In some embodiments, each of the plurality of nodes may be connected to a graphic representation of the corresponding at least one initial transcriptome data object, the corresponding at least one subsequent transcriptome data object, and/or the corresponding at least one clinical event data object.

Referring back to FIG. 11, subsequent to step/operation 1105, the example method 1100 proceeds to step/operation 1107. At step/operation 1107, a computing entity (such as the data object computing entity 105 described above in connection with FIG. 1 and FIG. 2) may include means (such as the processing element 205 of the data object computing entity 105 described above in connection with FIG. 2) to generate a risk window prediction data object based at least in part on providing the dynamic multigraph data object to the TGN.

For example, the processing element may provide the dynamic multigraph data object generated at step/operation 1105 to a TGN that has been trained to generate a risk window prediction data object (for example, based at least in part on those described in connection with at least FIG. 4 and FIG. 10). Based at least in part on the dynamic multigraph data object, the TGN may generate a risk window prediction data object corresponding to the dynamic multigraph data object.

In some embodiments, the TGN may calculate at least one differential expression metadata for example, based at least in part on at least those described above in connection FIG. 7 and FIG. 8 above). In such embodiments, the dynamic multigraph data object(s) provided to the TGN may not comprise the at least one differential expression metadata. The TGN may generate at least one risk window prediction data object based at least in part on the at least one differential expression metadata. For example, the TGN may compare genetic sequencing data (e.g. scRNA-seq assay metadata) at different points in time, thereby computing a temporal evolution of genetic expression in disease tissue that leads to the estimation of a time window of when the disease becomes onset.

Continuing from the example above, based at least in part on the dynamic multigraph data object, the TGN may generate a risk window prediction data object that indicates an estimated or predicted time frame that John will have onset NSCLC.

Referring back to FIG. 11, subsequent to step/operation 1107, the example method 1100 proceeds to step/operation 1109 and ends.

Referring now to FIG. 12, an example diagram 1200 is illustrated. In particular, the example diagram 1200 illustrates an example risk window prediction data object 1214 in connection with a dynamic multigraph data object.

In the example shown in FIG. 12, a processing element may generate a dynamic multigraph data object based at least in part on the initial transcriptome data object 1202, the WGS data object 1204, the subsequent transcriptome data object 1206, the clinical event data object 1208, the subsequent transcriptome data object 1210, and the clinical event data object 1212, similar to those described above. For example, the processing element may generate a node corresponding to an initial temporal identifier T0, and connect the node to a node representing the initial transcriptome data object 1202 and a node representing the WGS data object 1204, respectively. The processing element may generate a node corresponding to a subsequent temporal identifier T1, and connect the node to a node representing the subsequent transcriptome data object 1206 and the clinical event data object 1208, respectively. The processing element may generate a node corresponding to a subsequent temporal identifier T2, and connect the node to a node representing the subsequent transcriptome data object 1210 and the clinical event data object 1212, respectively.

As an example, the initial temporal identifier T0 may be associated with an index date for which PRS is generated for a disease, such as T1D. The clinical event data object 1208 may indicate an interaction with a care provider that identifies evidence of dysglycaemia, and the subsequent transcriptome data object 1206 may comprise scRNA-seq assay metadata associated with the interaction. The clinical event data object 1212 may indicate manifestation of clinical symptoms and signs of T1D (such as, but not limited to, polyuria diabetic ketoacidosis, polydipsia, etc.) during a clinical visit, and the subsequent transcriptome data object 1210 may comprise scRNA-seq assay metadata generated during the clinical visit.

In some embodiments, the processing element may provide the dynamic multigraph data object to a TGN, and the TGN may generate a risk window prediction data object 1214, similar to those described above.

In the example shown in FIG. 12, the risk window prediction data object 1214 may indicate a time frame of when the disease is predicted to be onset on the time axis. In some embodiments, the risk window prediction data object 1214 comprises an estimated lower bound metadata T1 and an estimated upper bound metadata Tu associated with the disease identifier. In some embodiments, the estimated lower bound metadata T1 indicates the earliest date that the disease is predicted to be onset, and the estimated upper bound metadata Tu indicates the latest date that the disease is predicted to be onset. In some embodiments, the processing element may generate a confidence interval associated with the risk window prediction data object. Additionally, or alternatively, the processing element may generate estimated probabilities for the estimated lower bound metadata T1 and the estimated upper bound metadata Tu.

V. CONCLUSION

Many modifications and other embodiments of the disclosure set forth herein will come to mind to one skilled in the art to which this disclosure pertain having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A system comprising memory and one or more processors communicatively coupled to the memory, the one or more processors configured to:
    receive a first initial transcriptome data object, validated onset temporal metadata, and a first subsequent transcriptome data object related to a disease identifier and associated with a first client profile data object, wherein the first subsequent transcriptome data object is associated with a clinical event data object and the validated onset temporal metadata comprises a timestamp that indicates a clinically validated time that a disease corresponding to the disease identifier was determined to be onset for the first client profile data object;
    receive a dynamic multigraph data object that corresponds to the disease identifier, wherein the dynamic multigraph data object comprises a plurality of nodes and a plurality of edges that correspond to a plurality of client profile data objects associated with the disease identifier;
    store the first initial transcriptome data object, the validated onset temporal metadata, the first subsequent transcriptome data object, and the clinical even data object as one or more nodes of the plurality of nodes within the dynamic multigraph data object, wherein the dynamic multigraph data object comprises one or more time axes that are associated with a temporal progression of the disease and the one or more nodes are linked to one or more temporal identifiers positioned on the one or more time axes;
    generate, using a temporal graph network (TGN) and based at least in part on the dynamic multigraph data object, a first risk window prediction data object that comprises an estimated lower bound metadata and an estimated upper bound metadata associated with the disease identifier;
    train the TGN until a time associated with the validated onset temporal metadata falls between the estimated lower bound metadata and the estimate upper bound metadata of the first risk window prediction data object, wherein the TGN is trained by:
        comparing the first risk window prediction data object with the time associated with the validated onset temporal metadata, and
        responsive to the time failing to fall between the estimated lower bound metadata and the estimated upper bound metadata of the first risk window prediction data object, adjusting one or more parameters of the TGN and regenerating the first risk window prediction data object;
    receive, via a user interface, an input that identifies a second client profile data object;
    store a second initial transcriptome data object and a second subsequent transcriptome data object that correspond to the second client profile data object within the dynamic multigraph data object;
    generate, using the TGN and based at least in part on the dynamic multigraph data object, a second risk window prediction data object; and
    render, using the user interface, the second risk window prediction data object.

2. The system of claim 1, wherein the first client profile data object is associated with a whole-genome sequence (WGS) data object comprising at least one of at least one polygenic risk score (PRS) metadata related to the disease identifier or at least one combined PRS and phenome-wide association study (PRS-PheWAS) metadata related to the disease identifier.

3. The system of claim 1, wherein the first initial transcriptome data object comprises initial transcriptome metadata related to one or more particular tissues or cells associated with the disease identifier, and wherein the first subsequent transcriptome data object comprises subsequent transcriptome metadata related to the one or more particular tissues or cells associated with the disease identifier.

4. The system of claim 3, wherein the first initial transcriptome data object comprises an initial single-cell ribonucleic acid (RNA) sequencing assay (scRNA-seq) metadata associated with the disease identifier, and wherein the first subsequent transcriptome data object comprises subsequent scRNA-seq assay metadata associated with the disease identifier.

5. The system of claim 3, wherein the one or more processors are further configured to:
    calculate differential expression metadata based at least in part on the first initial transcriptome data object and the first subsequent transcriptome data object; and
    generate the dynamic multigraph data object based at least in part on the differential expression metadata.

6. The system of claim 1, wherein the first client profile data object is associated with a whole-genome sequence (WGS) data object and the first initial transcriptome data object and the WGS data object are associated with an initial temporal identifier.

7. The system of claim 6, wherein the first subsequent transcriptome data object and the clinical event data object are associated with a subsequent temporal identifier.

8. The system of claim 7, wherein the one or more processors are further configured to:
    generate the dynamic multigraph data object based further on the initial temporal identifier and the subsequent temporal identifier.

9. The system of claim 1, wherein the one or more processors are further configured to:
    transmit the first risk window prediction data object to a client computing entity.

10. A computer-implemented method comprising:
receiving, by one or more processors, a first initial transcriptome data object, validated onset temporal metadata, and a first subsequent transcriptome data object related to a disease identifier and associated with a first client profile data object, wherein the first subsequent transcriptome data object is associated with a clinical event data object and the validated onset temporal metadata comprises a timestamp that indicates a clinically validated time that a disease corresponding to the disease identifier was determined to be onset for the first client profile data object;
receiving, by the one or more processors, a dynamic multigraph data object that corresponds to the disease identifier, wherein the dynamic multigraph data object comprises a plurality of nodes and a plurality of edges that correspond to a plurality of client profile data objects associated with the disease identifier;
storing, by the one or more processors, the first initial transcriptome data object, the validated onset temporal metadata, the first subsequent transcriptome data object, and the clinical event data object as one or more nodes of the plurality of nodes within the dynamic multigraph data object, wherein the dynamic multigraph data object comprises one or more time axes that are associated with a temporal progression of the disease and the one or more nodes are linked to one or more temporal identifiers positioned on the one or more time axes;
generating, by the one or more processor, using a temporal graph network (TGN), and based at least in part on the dynamic multigraph data object, a first risk window prediction data object that comprises an estimate lower bound metadata and an estimate upper bound metadata associated with the disease identifier;
training, by the one or more processor, the TGN until a time associated with the validated onset temporal metadata falls between the estimated lower bound metadata and the estimate upper bound metadata of the first risk window prediction data object, wherein the TGN is trained by:
comparing the first risk window prediction data object with the time associated with the validated onset temporal metadata, and
responsive to the time failing to fall between the estimated lower bound metadata and the estimated upper bound metadata of the first risk window prediction data object, adjusting one or more parameters of the TGN and regenerating the first risk window prediction data object;
receiving, by the one or more processors and via a user interface, an input that identifies a second client profile data object;
storing, by the one or more processors, a second initial transcriptome data object and a second subsequent transcriptome data object that correspond to the second client profile data object within the dynamic multigraph data object;
generating, by the one or more processors, using the TGN, and based at least in part on the dynamic multigraph data object, a second risk window prediction data object; and
rendering, by the one or more processors and using the user interface, the second risk window prediction data object.

11. The computer-implemented method of claim 10, wherein the first initial transcriptome data object comprises initial transcriptome metadata related to one or more particular tissues or cells associated with the disease identifier, and wherein the first subsequent transcriptome data object comprises subsequent transcriptome metadata related to the one or more particular tissues or cells associated with the disease identifier.

12. The computer-implemented method of claim 11, wherein the first initial transcriptome data object comprises an initial single-cell ribonucleic acid (RNA) sequencing assay (scRNA-seq) metadata associated with the disease identifier, and wherein the first subsequent transcriptome data object comprises a subsequent scRNA-seq assay metadata associated with the disease identifier.

13. The computer-implemented method of claim 11, further comprising:
calculating differential expression metadata based at least in part on the first initial transcriptome data object and the first subsequent transcriptome data object; and
generating the dynamic multigraph data object based at least in part on the differential expression metadata.

14. The computer-implemented method of claim 10, wherein the first client profile data object is associated with a whole-genome sequence (WGS) data object and the first initial transcriptome data object and the WGS data object are associated with an initial temporal identifier.

15. The computer-implemented method of claim 14, wherein the first subsequent transcriptome data object and the clinical event data object are associated with a subsequent temporal identifier.

16. One or more non-transitory computer-readable storage media including instructions that, when executed by one or more processors, cause the one or more processors to:
receive a first initial transcriptome data object, validated onset temporal metadata, and a first subsequent transcriptome data object related to a disease identifier and associated with a first client profile data object, wherein the first subsequent transcriptome data object is associated with a clinical event data object and the validated onset temporal metadata comprises a timestamp that indicates a clinically validated time that a disease corresponding to the disease identifier was determined to be onset for the first client profile data object;
receive a dynamic multigraph data object that corresponds to the disease identifier, wherein the dynamic multigraph data object comprises a plurality of nodes and a plurality of edges that correspond to a plurality of client profile data objects associated with the disease identifier;
store the first initial transcriptome data object, the validated onset temporal metadata, the first subsequent transcriptome data object, and the clinical even data object as one or more nodes of the plurality of nodes within the dynamic multigraph data object, wherein the dynamic multigraph data object comprises one or more time axes that are associated with a temporal progression of the disease and the one or more nodes are linked to one or more temporal identifiers positioned on the one or more time axes;
generate, using a temporal graph network (TGN) and based at least in part on the dynamic multigraph data object, a first risk window prediction data object that comprises an estimated lower bound metadata and an estimated upper bound metadata associated with the disease identifier;
train the TGN until a time associated with the validated onset temporal metadata falls between the estimated lower bound metadata and the estimate upper bound metadata of the first risk window prediction data object, wherein the TGN is trained by:
  comparing the first risk window prediction data object with the time associated with the validated onset temporal metadata, and
  responsive to the time failing to fall between the estimated lower bound metadata and the estimated upper bound metadata of the first risk window prediction data object, adjusting one or more parameters of the TGN and regenerating the first risk window prediction data object;
receive, via a user interface, an input that identifies a second client profile data object;
store a second initial transcriptome data object and a second subsequent transcriptome data object that correspond to the second client profile data object within the dynamic multigraph data object;
generate, using the TGN and based at least in part on the dynamic multigraph data object, a second risk window prediction data object; and
render, using the user interface, the second risk window prediction data object.

17. The system of claim 1, the one or more processors are further configured to:
update the dynamic multigraph data object responsive to generating one or more of: one or more additional clinical event data objects or one or more additional subsequent transcriptome data objects.

* * * * *

UNITED STATES PATENT AND TRADEMARK OFFICE
CERTIFICATE OF CORRECTION

PATENT NO. : 12,362,069 B2
APPLICATION NO. : 17/304066
DATED : July 15, 2025
INVENTOR(S) : Paul J. Godden It is certified that error appears in the above-identified patent and that said Letters Patent is hereby corrected as shown below:

In the Claims

In Column 49, Line 49, Claim 1, delete "even data" and insert -- event data --, therefor.
In Column 49, Line 65, Claim 1, delete "estimate upper" and insert -- estimated upper --, therefor.
In Column 51, Line 30, Claim 10, delete "processor," and insert -- processors, --, therefor.
In Column 51, Lines 33-34, Claim 10, delete "estimate lower" and insert -- estimated lower --, therefor.
In Column 51, Line 34, Claim 10, delete "estimate upper" and insert -- estimated upper --, therefor.
In Column 51, Line 36, Claim 10, delete "processor," and insert -- processors, --, therefor.
In Column 51, Line 39, Claim 10, delete "estimate upper" and insert -- estimated upper --, therefor.
In Column 52, Line 51, Claim 16, delete "even data" and insert -- event data --, therefor.
In Column 52, Line 67, Claim 16, delete "estimate upper" and insert -- estimated upper --, therefor.

Signed and Sealed this
Fourteenth Day of October, 2025

John A. Squires
*Director of the United States Patent and Trademark Office*